US011881229B2

(12) United States Patent
Han et al.

(10) Patent No.: US 11,881,229 B2
(45) Date of Patent: Jan. 23, 2024

(54) SERVER FOR PROVIDING RESPONSE MESSAGE ON BASIS OF USER'S VOICE INPUT AND OPERATING METHOD THEREOF

(71) Applicant: Samsung Electronics Co., Ltd., Gyeonggi-do (KR)

(72) Inventors: Minseok Han, Gyeonggi-do (KR); Gahee Lee, Gyeonggi-do (KR); Yuri Choi, Gyeonggi-do (KR)

(73) Assignee: Samsung Electronics Co., Ltd.

( * ) Notice: Subject to any disclaimer, the term of this patent is extended or adjusted under 35 U.S.C. 154(b) by 528 days.

(21) Appl. No.: 17/269,188

(22) PCT Filed: Aug. 16, 2019

(86) PCT No.: PCT/KR2019/010448
§ 371 (c)(1),
(2) Date: Feb. 17, 2021

(87) PCT Pub. No.: WO2020/036467
PCT Pub. Date: Feb. 20, 2020

(65) Prior Publication Data
US 2021/0272585 A1 Sep. 2, 2021

(30) Foreign Application Priority Data
Aug. 17, 2018 (KR) .................. 10-2018-0096283

(51) Int. Cl.
*G10L 15/22* (2006.01)
*G10L 25/66* (2013.01)
(Continued)

(52) U.S. Cl.
CPC ............ *G10L 25/66* (2013.01); *A61B 5/4803* (2013.01); *G06F 40/30* (2020.01); *G06F 40/40* (2020.01);
(Continued)

(58) Field of Classification Search
CPC .......... G10L 15/22; G10L 15/00; G10L 15/01; G10L 15/06; G10L 15/063; G10L 15/08;
(Continued)

(56) References Cited

U.S. PATENT DOCUMENTS 8,156,062 B2  4/2012  Cho et al.
9,965,443 B2  5/2018  Eggink et al.
(Continued)

FOREIGN PATENT DOCUMENTS

JP  2012-518203  8/2012
JP  2017-196314  11/2017
(Continued)

OTHER PUBLICATIONS

KR Decision to Refuse dated Feb. 27, 2023 issued in counterpart application No. 10-2018-0096283, 6 pages.
(Continued)

*Primary Examiner* — Qi Han
(74) *Attorney, Agent, or Firm* — The Farrell Law Firm, P.C.

(57) ABSTRACT

Provided are a server for providing a response message, based on a voice input of a user, and an operation method of the server. Provided are a server that recognizes health state information of a user, based on a voice input from the user, analyzes pre-stored health data, generates a response message, based on the analyzed health data, and outputs the generated response message, and an operation method of the server.
Provided are a server that recognizes event information of a user from a voice input from the user, generates a response message, based on information about the type and frequency of a recognized event, and provides the generated response message, and an operation method of the server.

15 Claims, 24 Drawing Sheets

(51) Int. Cl.
  *G16H 10/60* (2018.01)
  *G16H 15/00* (2018.01)
  *G16H 50/30* (2018.01)
  *G16H 50/70* (2018.01)
  *G16H 50/20* (2018.01)
  *G06F 40/40* (2020.01)
  *G06F 40/30* (2020.01)
  *A61B 5/00* (2006.01)
  *G06N 5/043* (2023.01)
  *G10L 15/18* (2013.01)
  *G10L 15/30* (2013.01)
  *H04L 51/046* (2022.01)
  *G16H 40/67* (2018.01)
  *G06N 20/00* (2019.01)

(52) U.S. Cl.
  CPC .......... *G06N 5/043* (2013.01); *G10L 15/1815* (2013.01); *G10L 15/22* (2013.01); *G10L 15/30* (2013.01); *G16H 10/60* (2018.01); *G16H 15/00* (2018.01); *G16H 50/20* (2018.01); *G16H 50/30* (2018.01); *G16H 50/70* (2018.01); *H04L 51/046* (2013.01); *G06N 20/00* (2019.01); *G16H 40/67* (2018.01)

(58) Field of Classification Search
  CPC ..... G10L 15/14; G10L 15/18; G10L 15/1815; G10L 15/1822; G10L 15/183; G10L 15/24; G10L 15/26; G10L 15/30; G10L 2015/0631–0638; G10L 2015/221–228

USPC .... 704/270.1, 270, 272, 275, 231, 235, 251, 704/257

See application file for complete search history.

(56) References Cited

U.S. PATENT DOCUMENTS

| | | | |
|---|---|---|---|
| 10,020,076 B1* | 7/2018 | Anumalasetty | G16H 10/60 |
| 2014/0316285 A1 | 10/2014 | Dossas et al. | |
| 2017/0277854 A1* | 9/2017 | Kelly | G16Z 99/00 |
| 2019/0043501 A1* | 2/2019 | Ramaci | G16H 40/20 |
| 2019/0043622 A1* | 2/2019 | Ramaci | G06F 1/163 |
| 2019/0060163 A1 | 2/2019 | Roth | |

FOREIGN PATENT DOCUMENTS

| | | |
|---|---|---|
| KR | 1020030033890 | 5/2003 |
| KR | 10-1364851 | 2/2014 |
| KR | 10-1775490 | 9/2017 |
| KR | 1020180042702 | 4/2018 |

OTHER PUBLICATIONS

European Search Report dated Nov. 27, 2019 issued in counterpart application No. PCT/KR2019/010448, 17 pages.

Korean Office Action dated Aug. 11, 2022 issued in counterpart application No. 10-2018-0096283, 11 pages.

* cited by examiner

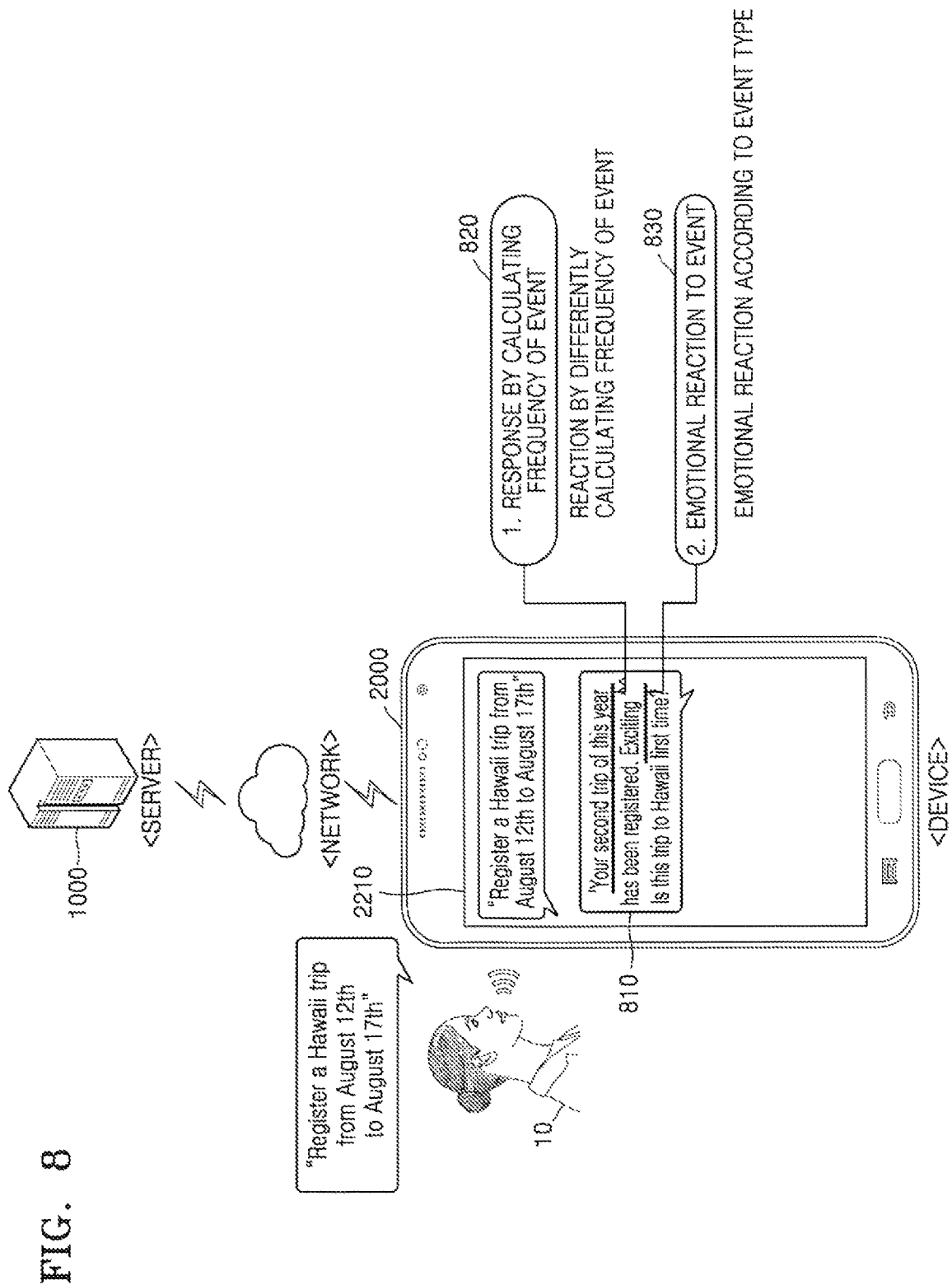

FIG. 11

| Event type (1110) | Frequency item (1120) | Frequency calculation cycle and method (1130) | Exemplary response (1140) | Accuracy improvement and personalization method (1150) |
|---|---|---|---|---|
| Travel | Travel frequency | Sequential order of travel during one year based on registered date | "This is the third trip in this year" "This is the last trip of 2018. Exciting ∧∧" | "I can see from the gallery that you have gone on a second trip to Daegwallyeong" |
| Travel | Place frequency | Sequential order of visit to registered place | "Is this trip to Pusan first time ?" "This is the first visit to Sydney together with Bixby." | |
| Wedding anniversary Birthday | Corresponding event frequency | Every year based on Wedding/birth year | The date is the second wedding anniversary !" "The data is 27th anniversary. Congratulations" | "Is the date the first wedding anniversary ?" "What year were you married ? I can inform you of what year anniversary is this year." |
| Exercise | Exercise frequency | Sequential order in units of weeks/months | "That is the third exercise this week" "That is the eighth exercise of July. OO who tries to exercise consistently is cool !" | (at the ending time of the schedule) "Have you just finished Yoga ? I will reflect this time Yoga on the exercise frequency" |
| Meeting | Person/Meeting encounter frequency | Calculation of meeting cycle | "That is an appointment with Younghee in one month" "That is a mountain-hiking club meeting in two months" | |
| Conference | Conference frequency | Per day/week | "There is the last conference schedule of Friday. There were seven conferences for one week. Weekend is coming soon, so let's cheer up!" | |

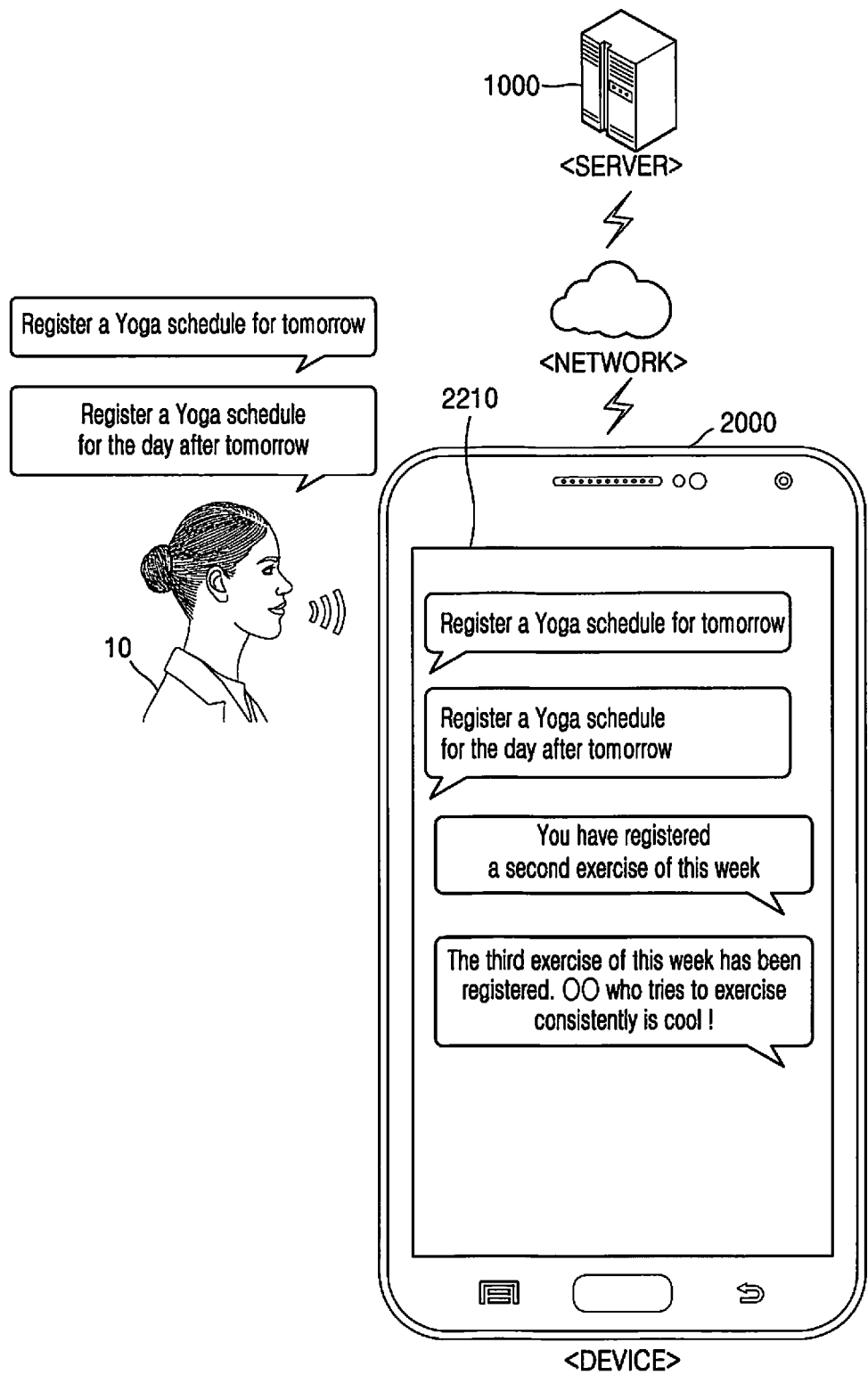

SERVER FOR PROVIDING RESPONSE MESSAGE ON BASIS OF USER'S VOICE INPUT AND OPERATING METHOD THEREOF

PRIORITY

This application is a National Phase Entry of PCT International Application No. PCT/KR2019/010448 which was filed on Aug. 16, 2019, and claims priority to Korean Patent Application No. 10-2018-0096283, which was filed on Aug. 17, 2018, the content of each of which is incorporated herein by reference.

TECHNICAL FIELD

The present disclosure relates to servers for providing a response message, based on a voice input of a user, and operation methods thereof, and more particularly, to a server connected to an interactive device through a network to recognize state information, such as health information or event information of a user, from a voice input of a user and generate and provide a response message according to the recognized state information of the user, and an operation method of the server.

BACKGROUND ART

With the development of multimedia technology and networking technology, users have been able to receive various services by using devices. In particular, with the development of speech recognition technology, a user has been able to input a voice input to a device and execute an operation of the device according to the voice input.

However, in the conventional art, it is difficult to accurately ascertain the intention of a user from a voice input of the user, and, even when the intention of the user is ascertained, it is hard to give appropriate feedback to the user. Thus, there is demand for a technology of ascertaining the intention of a user from a voice input of the user and effectively recommending the user to perform a replacement operation of an operation requested by the user.

In particular, with the recent development of technology such as artificial intelligence (AI) (for example, deep learning), an intelligent service that automatically recognizes data such as a voice, an image, a moving picture, or text and provides information related to the data or provides a service related to the data is being used in various fields.

AI systems are computer systems configured to realize human-level intelligence, and train themselves and make determinations spontaneously to become smarter, in contrast to existing rule-based smart systems. Because recognition rates of AI systems improve and the AI systems more accurately understand a user's preferences the more they are used, existing rule-based smart systems are being gradually replaced by deep-learning AI systems.

AI technology includes machine learning (e.g., deep learning) and element technologies employing the machine learning.

Machine learning is an algorithm technology that self-classifies/learns the characteristics of input data, and each of the element technologies is a technology of mimicking functions of human brains, such as perception and determination, by using a machine learning algorithm, such as deep learning, and includes technical fields, such as linguistic understanding, visual understanding, inference/prediction, knowledge representation, and operation control.

Various fields to which AI technology is applied are as follows. Linguistic understanding is a technique of recognizing a language/character of a human and applying/processing the language/character of a human, and includes natural language processing, machine translation, a conversation system, questions and answers, voice recognition/synthesis, and the like. Visual understanding is a technique of recognizing and processing an object like in human vision, and includes object recognition, object tracking, image search, human recognition, scene understanding, space understanding, image improvement, and the like. Inference/prediction is a technology of logically performing inference and prediction by determining information, and includes knowledge/probability-based inference, optimization prediction, a preference-based plan, recommendation, and the like. Knowledge representation is a technique of automatically processing human experience information as knowledge data, and includes knowledge establishment (data generation/classification), knowledge management (data utilization), and the like. Operation control is a technique of controlling autonomous driving of a vehicle and motions of a robot, and includes motion control (navigation, collision avoidance, and driving), manipulation control (behavior control), and the like.

Recently, devices including an interactive artificial assistant that performs a specific action or provides an answer according to a user's voice input by using AI technology are being utilized. The interactive artificial assistant may perform a pre-stored answer or action according to a question or instruction of a user. However, because the interactive artificial assistant simply repeatedly uses a certain phrase from among phrases previously stored in a memory or a server, the user does not feel that the interactive artificial assistant recognizes the user.

DESCRIPTION OF EMBODIMENTS

Solution to Problem

Provided are a server that recognizes state information of a user from a voice input from the user, analyzes health state information of the user, generates a response message, based on the analyzed health state information, and provides the generated response message, and an operation method thereof.

Provided are a server that recognizes event information of a user from a voice input from the user, generates a response message, based on information about the type and frequency of the recognized event, and provides the generated response message, and an operation method thereof.

Advantageous Effects of Disclosure

Recognition of the health state of a user or event information of the user and outputting of a response message according to the recognized health state or event information through a device enable a user to feel that the device recognizes the user and provides an emotionally sympathetic response.

BRIEF DESCRIPTION OF DRAWINGS

This disclosure may be readily understood by reference to the following detailed description and the accompanying drawings, in which reference numerals refer to structural elements:

FIG. 8 is a view illustrating an example in which a device according to an embodiment of the disclosure outputs a response message, based on event information of a user;

FIG. 11 is a table showing an example of a response message generated by a server according to an embodiment of the present disclosure, based on the types of events and the frequencies of the events;

FIGS. 12A through 12C are views illustrating examples in which a device according to an embodiment of the present disclosure registers event information, based on a voice input of a user, and outputs a response message, based on the registered event information;

BEST MODE

Figure 1:
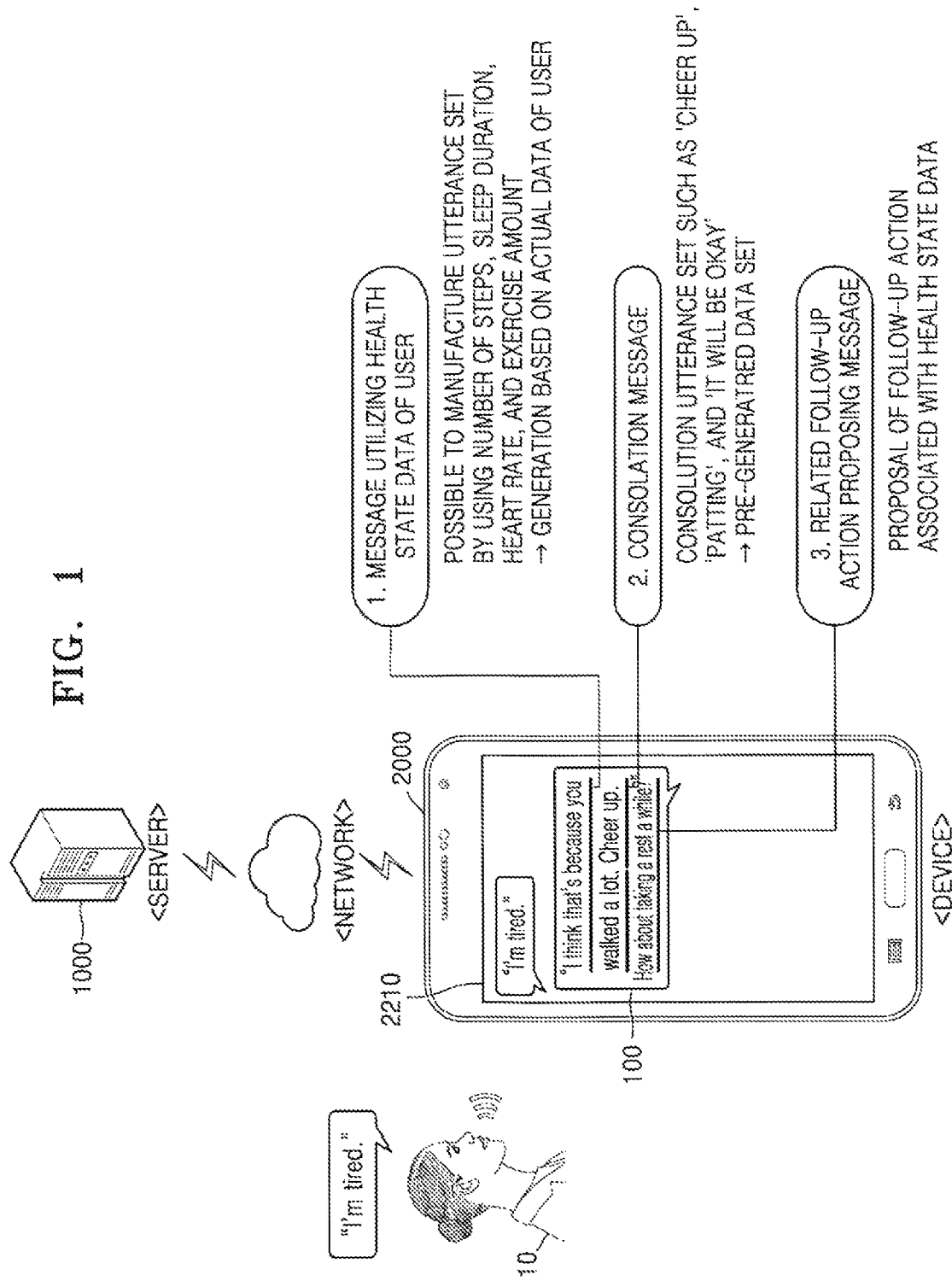
FIG. 1 is a view illustrating an example in which a device according to an embodiment of the disclosure outputs a response message with respect to a voice input of a user.

According to an aspect of the present disclosure, a method, performed by a server, of providing a response message for a voice input of a user includes the operations of receiving a voice input of a user from a device, converting the received voice input into text by performing automatic speech recognition (ASR), recognizing a health state of the user by interpreting the text by using a natural language understanding (NLU) model, analyzing health data associated with the recognized health state from among pre-stored health data of the user, generating a response message including a first message regarding the recognized health state and the analyzed health data, a second message providing an emotional consolation to the user, and a third message proposing a follow-up action associated with the analyzed health data, by using a natural language generator (NLG), and providing the generated response message to the device so that the generated response message is output through the device.

According to another aspect of the present disclosure, a server for providing a response message for a voice input of a user includes a communication interface configured to perform data communication with a device, a storage accumulating and storing health data of the user, a memory storing a program including one or more instructions, and a processor configured to execute the one or more instructions stored in the memory. The processor controls the communication interface to receive the voice input of the user from the device, converts the received voice input into text by using an ASR model, recognizes a health state of the user by interpreting the text by using an NLU model, analyzes health data associated with the recognized health state from among the health data of the user pre-stored in the storage, generates a response message including a first message regarding the recognized health state and the analyzed health data, a second message providing an emotional consolation to the user, and a third message proposing a follow-up action associated with the analyzed health data, by using an NLG, and provides the generated response message to the device through the communication interface.

According to another aspect of the present disclosure, a non-transitory computer-readable recording medium has recorded thereon a computer program. The computer-readable recording medium includes instructions of performing the operations of providing a response message for a voice input of a user includes the operations of receiving a voice input of a user from a device, converting the received voice input into text by performing ASR, recognizing a health state of the user by interpreting the text by using an NLU model, analyzing health data associated with the recognized health state from among pre-stored health data of the user, generating a response message including a first message regarding the recognized health state and the analyzed health data, a second message providing an emotional consolation to the user, and a third message proposing a follow-up action associated with the analyzed health data, by using an NLG, and providing the generated response message to the device so that the generated response message is output through the device.

Mode of Disclosure

The present application is based on and claims priority to Korean Patent Application No. 10-2018-0096283, filed on Aug. 17, 2018, in the Korean Intellectual Property Office.

Although general terms widely used at present were selected for describing the present disclosure in consideration of the functions thereof, these general terms may vary according to intentions of one of ordinary skill in the art, case precedents, the advent of new technologies, or the like. Terms arbitrarily selected by the applicant of the disclosure may also be used in a specific case. In this case, their meanings need to be given in the detailed description. Hence, the terms must be defined based on their meanings and the contents of the entire specification, not by simply stating the terms.

The terms "comprises" and/or "comprising" or "includes" and/or "including" when used in this specification, specify the presence of stated elements, but do not preclude the presence or addition of one or more other elements. The terms "unit", "-er(-or)", and "module" when used in this specification refers to a unit in which at least one function or operation is performed, and may be implemented as hardware, software, or a combination of hardware and software.

In this specification, 'natural language understanding' is a model trained to interpret text into which a voice input is converted. According to an embodiment, a natural language understanding model may be trained to recognize a health state of a user or recognize event information of the user.

In this specification, a 'natural language generator' is a model trained to generate a response message for a voice input of a user by combining pre-stored morphemes, words, or phrases. According to an embodiment, the natural language generator may generate a response message associated with a health state of the user or event information of the user analyzed by natural language understanding.

In this specification, 'health data' refers to information including at least one of biometric information, exercise information, and sleep information of the user collected by a device. According to an embodiment, the device may transmit health data to a server, and the server may store the health data. According to an embodiment, when the server obtains health data from the device, the server may also obtain device identification (ID) information of the device (e.g., a device ID) and account information of a user of the device (e.g., a user ID), and may store the health data according to the device ID information and the account information of the user.

Examples are described in detail herein with reference to the accompanying drawings so that this disclosure may be easily performed by one of ordinary skill in the art to which the disclosure pertain. The disclosure may, however, be embodied in many different forms and should not be construed as being limited to the examples set forth herein.

Embodiments of the disclosure now will be described more fully hereinafter with reference to the accompanying drawings.

FIG. 1 is a view illustrating an example in which a server 1000 according to an embodiment of the disclosure provides a response message to a device 2000, based on a voice input of a user.

Referring to FIG. 1, the device 2000 may receive a voice input from a user 10 through a microphone, and transmit the voice input to the server 1000. According to an embodiment, the device 2000 may obtain a sound signal from the received voice input and may transmit the speech signal to the server 1000.

The server 1000 may generate a response message 100, based on the received voice input, and may transmit the generated response message to the device 2000. The device 2000 may output the response message 100 received from the server 1000. According to an embodiment, the device 2000 may output a response message 100 composed of a character, text, a graphical user interface (GUI), or a combination thereof, through a display 2210 of FIG. 16.

Figure 17:
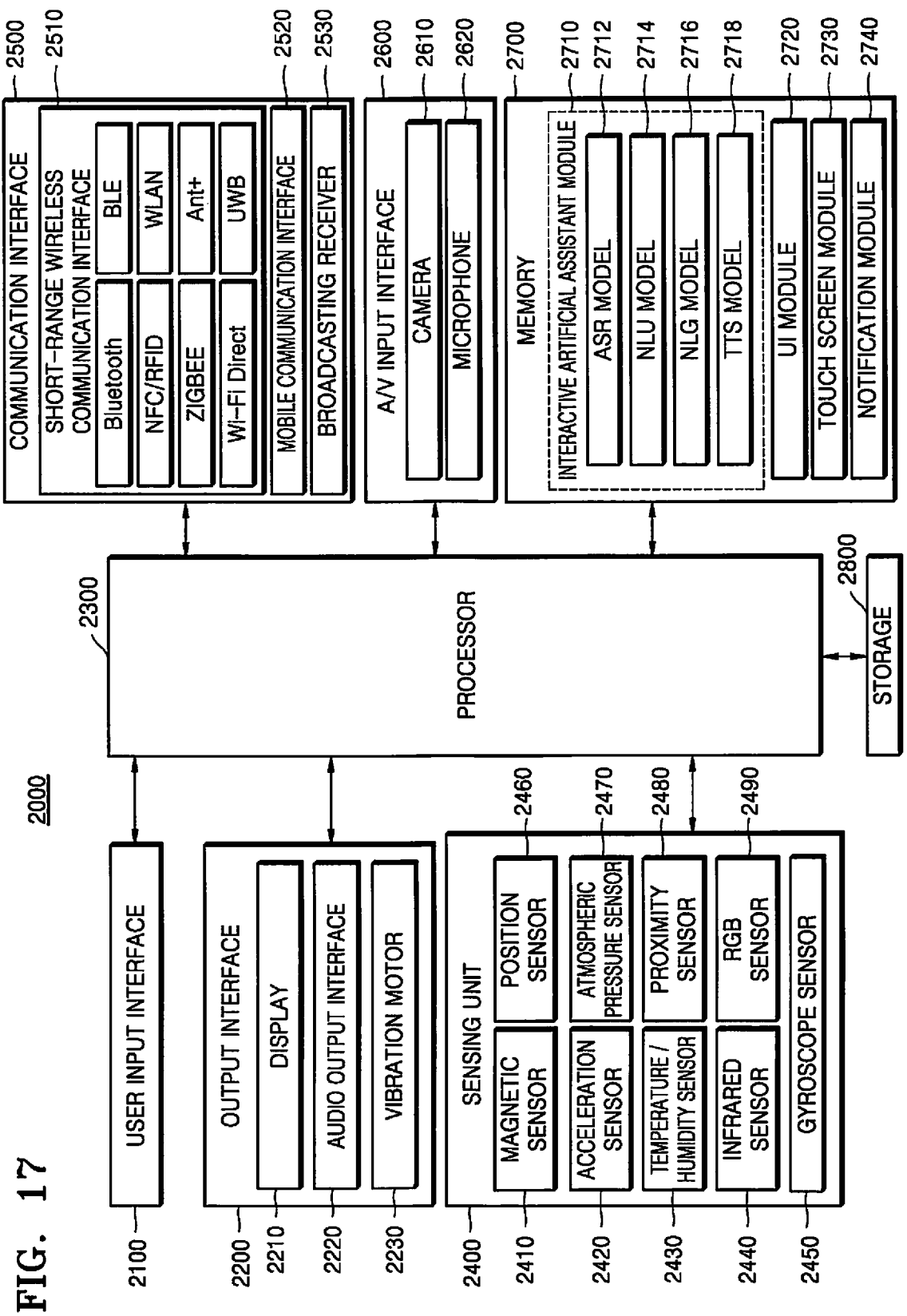
FIG. 17 is a block diagram of a structure of a device according to an embodiment of the present disclosure.

According to an embodiment, the device 2000 may output the response message 100 through an audio output interface 2220 of FIG. 17. In this case, the server 1000 may convert the response message 100 having a text form into an audio signal, by using a text to speech (TTS) model.

The server 1000 may convert the voice input received from the device 2000 into computer-readable text by performing automatic speech recognition (ASR). The server 1000 may interpret the computer-readable text, and recognize a health state of the user, based on a result of the interpretation, by using a natural language understanding (NLU) model.

The server 1000 may analyze health data associated with the recognized health state from pre-stored health data of the user, and may generate the response message 100, based on a result of the analysis. The health data may include, for example, at least one of the number of steps taken by the user, a sleep duration of the user, a heart rate thereof, or an exercise amount thereof. The server 1000 may generate a response message by using a natural language generator (NLG).

According to an embodiment, the server 1000 may generate the response message 100 including a consolation message corresponding to the voice input of the user. The consolation message may be a message that provides emotional consolation to the user, such as 'Cheer up', 'Patting', or 'It will be okay'. The consolation message may be obtained through a pre-stored data set.

According to an embodiment, the server 1000 may generate the response message 100 including a message that proposes a follow-up action associated with the health state information of the user.

A server or device including a conventional interactive artificial assistant using AI technology only performs a previously-stored answer or operation with respect to a voice input including a user's question or instruction. Because the conventional interactive artificial assistant simply repeatedly uses a certain phrase from among phrases previously stored in a memory or a server, a user does not feel that the interactive artificial assistant recognizes the user.

The server 1000 according to an embodiment of the present disclosure may analyze health state information of the user, based on the voice input of the user obtained through the device 2000, generate the response message 100 including a message based on the health state information of the user, a consolation message that provides emotional consolation to the user, and a message that proposes a follow-up action associated with the health state information, provide the generated response message 100 to the device 2000, and may output the response message 100 through the device 2000. Accordingly, the user may receive a feeling that the device 2000 recognizes the user himself or herself and provides an emotionally sympathetic response.

Figure 2:
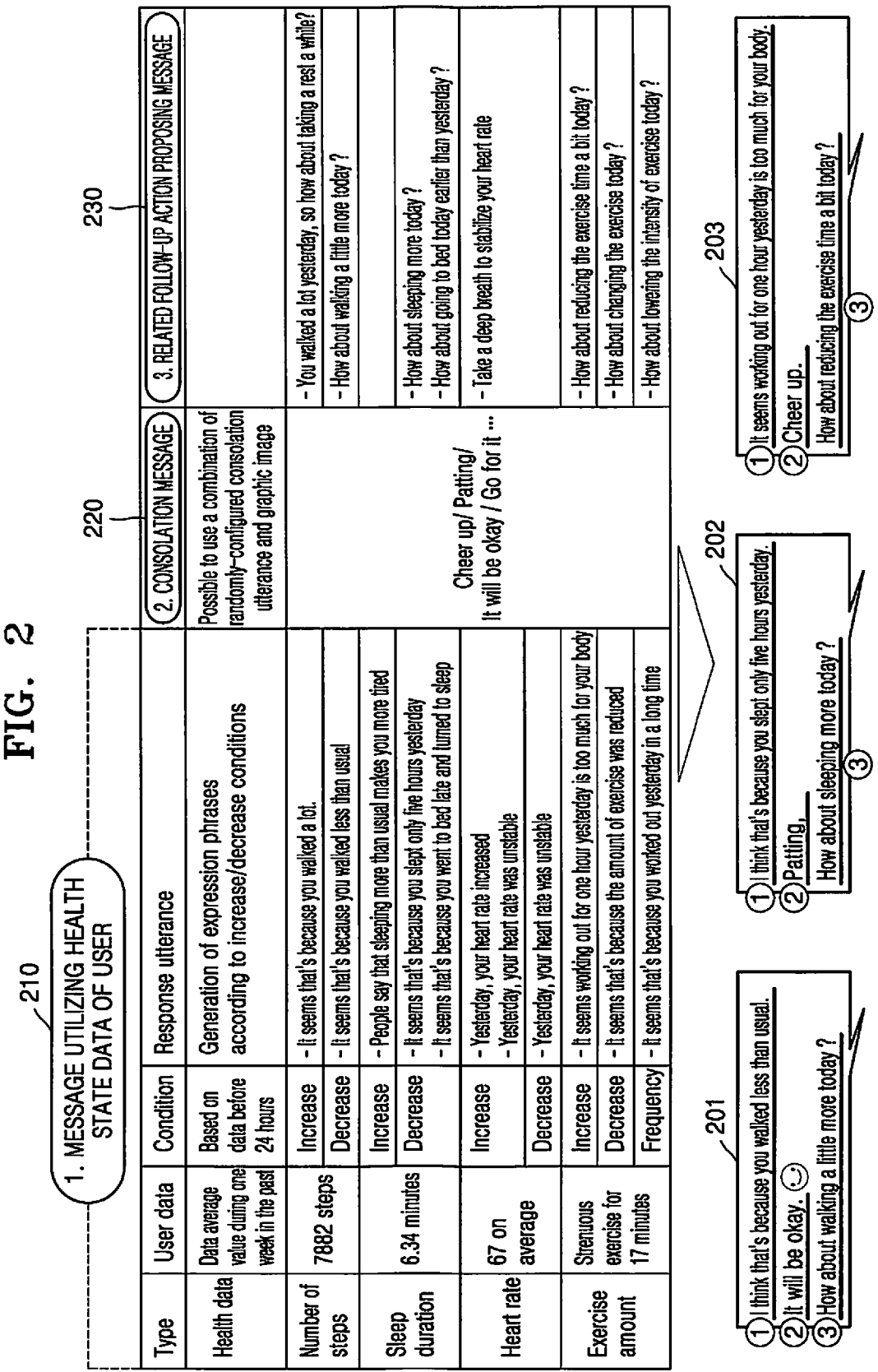
FIG. 2 is a table showing an example of a response message generated by a server according to an embodiment of the present disclosure, based on health state information of a user.

FIG. 2 is a table showing an example of a response message generated by the server 1000 according to an embodiment of the present disclosure, based on the health state information of the user.

Referring to FIG. 2, the server 1000 may provide a response message including a first message 210 utilizing health state data of the user, a second message 220 as a consolation message that provides emotional consolation to the user, and a third message 230 proposing a follow-up action associated with the health state data.

Figure 16:
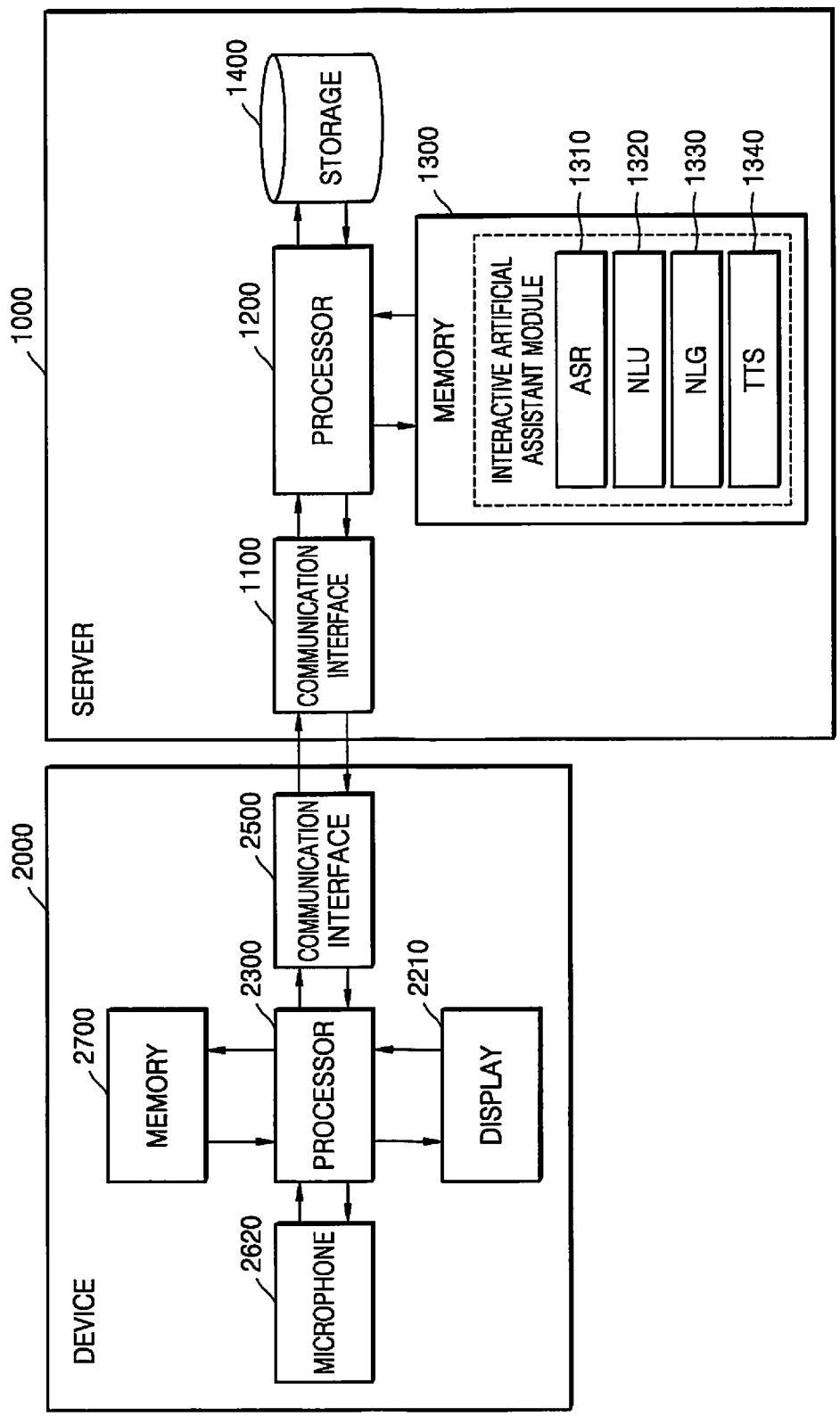
FIG. 16 is a block diagram of structures of a server and a device according to an embodiment of the present disclosure.

The server 1000 may obtain health data including at least one of the number of steps taken by the user, a sleep duration of the user, a heart rate thereof, and an exercise amount thereof from the device 2000, and may store the obtained health data to a storage 1400 of FIG. 16. According to an embodiment, the server 1000 may also obtain device ID information of the device 2000 (e.g., a device ID), and account information of the user of the device 2000 (e.g., a user ID) when obtaining health data from the device 2000, and may store the health data according to the device ID information and the account information of the user.

The first message 210 may be generated based on user information and conditions according to the type of health data. According to an embodiment, the server 1000 may obtain health data including the number of steps, a sleep duration, a heart rate, and an exercise amount from the device 2000 of the user, and may generate the first message 210, based on information of the user and condition information of the user according to the type of health data. For example, when the type of health data is the number of steps and the user takes more steps within 24 hours from the time point when the device 2000 receives the voice input of the user than 7882 steps taken on the average before one week from the time point when the device 2000 receives the voice input of the user, the server 1000 may generate a first message 210 of 'I think that's because you walked a lot'. In the opposite case, namely, when the user takes less steps within 24 hours from the time point when the device 2000 receives the voice input of the user than 7882 steps, the server 1000 may generate a first message 210 of 'I think that's because you walked less than usual'.

The second message 220 may be generated by selecting one of pre-stored consolation messages regardless of the health state information of the user. According to an embodiment, the server 1000 may generate the second message 220 by randomly selecting one of the pre-stored consolation messages. According to an embodiment, the server 1000 may generate the second message 220 composed of a combination of a consolation message and a graphic image. For example, the second message 220 may include a randomly-selected consolation message and an emoticon. The second message 220 may include a consolation comment such as 'Cheer up', 'Patting', 'It will be okay', or 'Go for it'.

The third message 230 may include a message that proposes a follow-up action associated with health-related information of the user. According to an embodiment, the server 1000 may generate the third message 230 proposing a follow-up action associated based on health information and conditions according to the type of health data. For example, when the type of health data is the number of steps and the user takes more steps within 24 hours from the time point when the device 2000 receives the voice input of the user than 7882 steps taken on the average before one week from the time point when the device 2000 receives the voice input of the user, the server 1000 may generate a third message 230 proposing a rest, such as 'You walked a lot yesterday, so how about taking a rest a while?'. In the opposite case, namely, when the user takes less steps within 24 hours from the time point when the device 2000 receives the voice input of the user than 7882 steps, the server 1000 may generate a third message 230 proposing a follow-up action of increasing the number of steps, such as 'How about walking more today?'.

FIG. 2 illustrates an example of a response message generated by the server 1000. A first response message 201 may include a first message generated based on health-related information and conditions of the user, such as 'I think that's because you walked less than usual', a second message as a consolation message such as 'It will be okay', and a third message proposing a follow-up action, such as 'How about walking a little more today?'.

Similarly, a second response message 202 may include a first message generated based on health-related information and conditions of the user, such as 'I think that's because you slept only five hours yesterday', a second message as a consolation message such as 'Patting', and a third message proposing a follow-up action, such as 'How about sleeping more today?'. A third response message 203 may include a first message generated based on health-related information and conditions of the user, such as 'It seems working out for one hour yesterday is too much for your body', a second message as a consolation message such as 'Cheer up', and a third message proposing a follow-up action, such as 'How about reducing the exercise time a bit today?'.

Figure 3A:
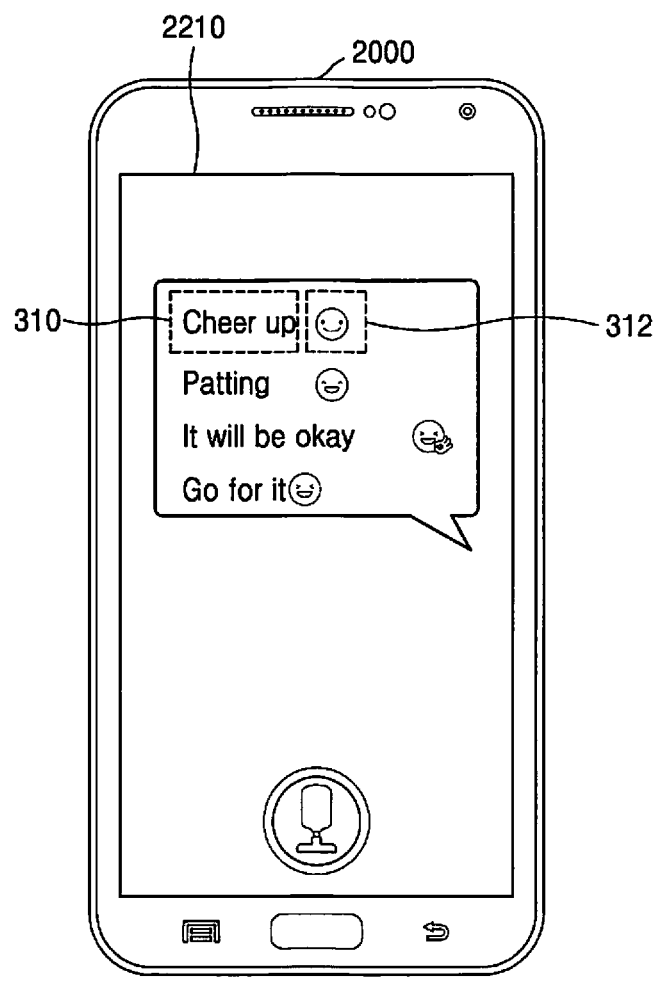
FIGS. 3A through 3C illustrate examples in which a device according to an embodiment of the present disclosure outputs a response message generated based on a health state of a user.
Figure 3B:
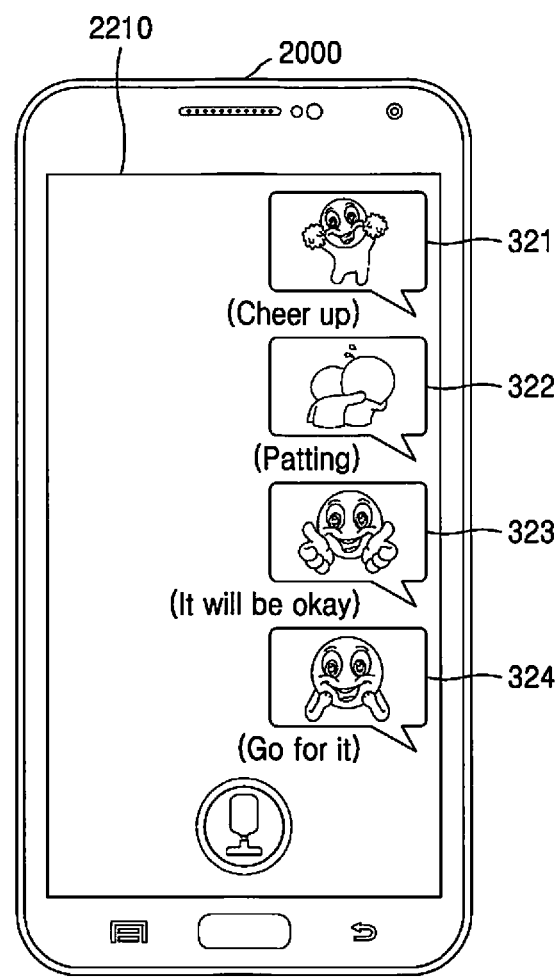
Figure 3C:
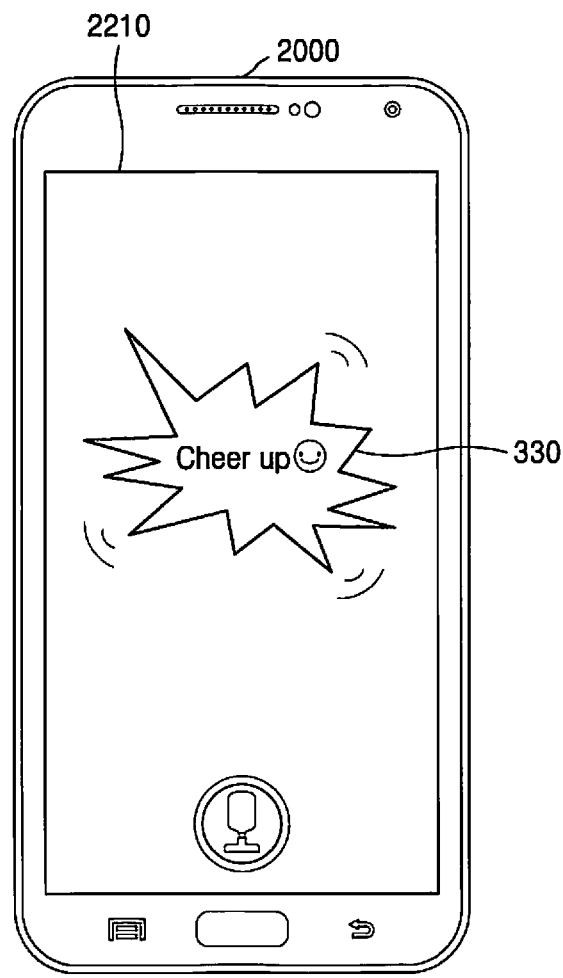

FIGS. 3A through 3C illustrate examples in which the device 2000 according to an embodiment of the present disclosure outputs a response message generated based on a health state of a user.

Referring to FIG. 3A, the device 2000 may display a consolation message together with a graphic image such as an emoticon, on the display 2210. For example, the device 2000 may display a consolation message 310 such as 'Cheer up' together with an emoticon 312 representing the face shape of a smiling person, on the display unit 2210.

Referring to FIG. 3B, the device 2000 may display only a graphic image, rather than a consolation message composed of a character or text, on the display 2210. For example, a first image 321 may be an image corresponding to 'Cheer up'. A second image 322 may be an image corresponding to 'Patting', a third image 323 may be an image corresponding to 'It will be okay', and a fourth image 324 may be an image corresponding to 'Go for it'.

Referring to FIG. 3C, the device 2000 may apply a visual effect to a consolation message composed of text, and display the visual effect on the display 2210. For example, the device 2000 may apply a visual effect, such as shaking of text representing a consolation message, changing of the color of a speech balloon including the consolation message, changing of the text color of the consolation message, or changing of the text size of the consolation message, to the consolation message, and may display the consolation message to which the visual effect has been applied on the display 2210.

Figure 4:
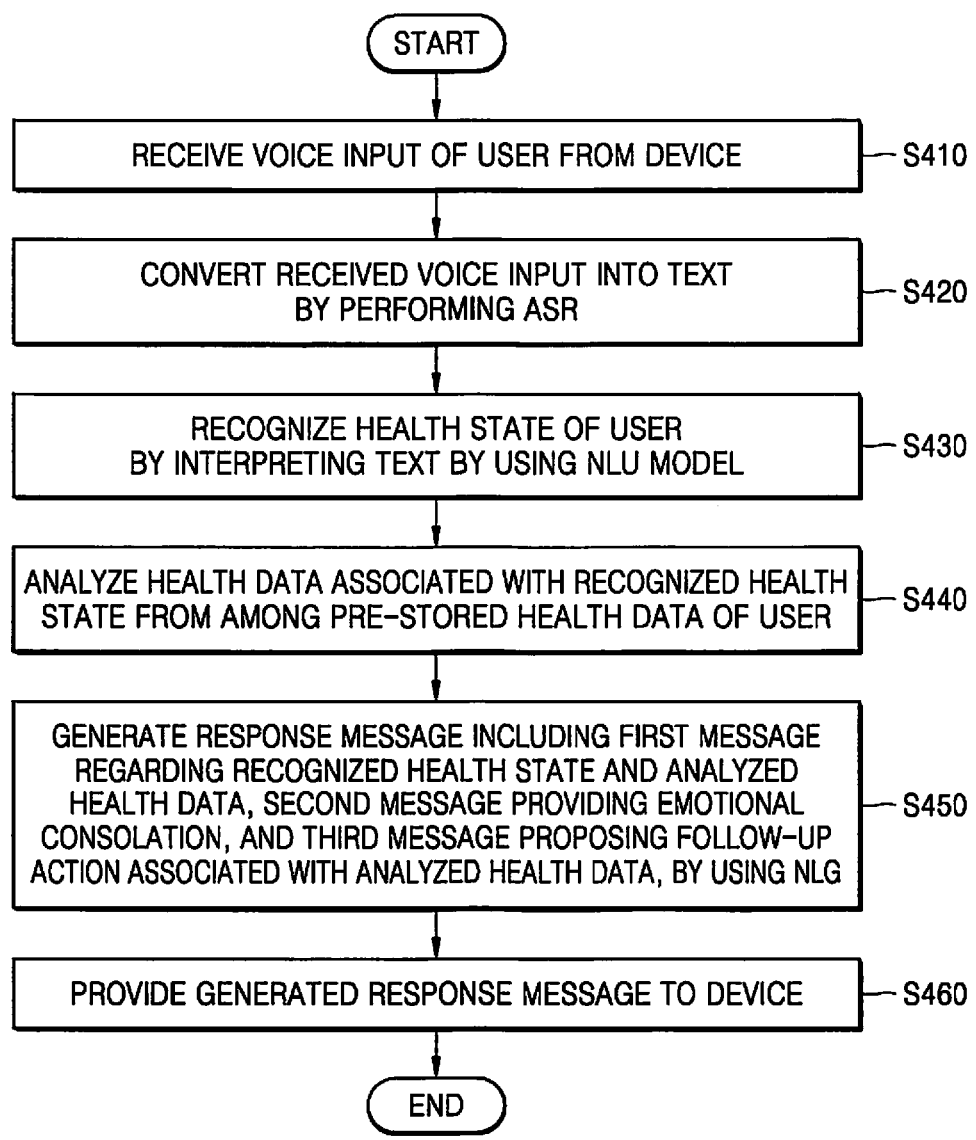
FIG. 4 is a flowchart of a method, performed by a server according to an embodiment of the present disclosure, of providing a response message, based on a voice input of a user.

FIG. 4 is a flowchart of a method, performed by the server 1000 according to an embodiment of the present disclosure, of providing a response message, based on a voice input of a user.

In operation S410, the server 1000 receives the voice input of the user from the device 2000. According to an embodiment, the device 2000 may obtain the voice input of the user through a microphone, and may transmit the obtained voice input to the server 1000. According to an embodiment, the server 1000 may obtain ID information (e.g., ID information) of the device 2000 or account information of the user (e.g., the ID of the user) from the device 2000. According to an embodiment, in response to the ID information of the device 2000, the server 1000 may search for the account information of the user associated with the ID information of the device 2000.

In operation S420, the server 1000 converts the received voice input into text by performing ASR. According to an embodiment, the server 1000 may perform an ASR operation of converting a voice input into computer-readable text by using a predefined model such as an acoustic model (AM) or a language model (LM). When the server 1000 receives a sound signal from which noise has not been removed from the device 2000, the server 1000 may obtain an audio signal by removing noise from the received sound signal, and may perform ASR on the audio signal.

In operation S430, the server 1000 recognizes a health state of the user by interpreting the text by using the NLU model. According to an embodiment, the server 1000 may recognize the health state of the user from the text by performing syntactic analysis or semantic analysis by using the NLU model. According to an embodiment, the server 1000 may parse the text in units of morphemes, words, or phrases and may infer the meaning of a word extracted from the parsed text by using linguistic characteristics (e.g., a syntactic element) of the parsed morpheme, word, or phrase, by using the NLU model. The server 1000 may determine a health state corresponding to the inferred meaning of the word, by comparing the inferred meaning of the word with pieces of data about pre-defined health states provided by the NLU model. For example, the server 1000 may recognize a current health state of the user by interpreting text such as 'I'm tired', 'Sleepy', 'My legs hurt', or 'I feels low'.

In operation S440, the server 1000 analyzes health data associated with the recognized health state from among pre-stored health data of the user. According to an embodiment, the server 1000 may analyze health data associated with the recognized health state from among a plurality of types of pre-stored health data. According to an embodiment, the server 1000 may analyze the change degree of recent health data from among the pre-stored health data, by comparing the recent health data with an average value of health data accumulated during a time section from the moment when the device 2000 receives the voice input to a preset time. According to an embodiment, the server 1000 may analyze the change degree of health data, by obtaining recent health data including information of the user and condition information for each type of health data, such as the number of steps, a sleep duration, a heart rate, and an exercise amount at a specific time point, and comparing the obtained recent health data with accumulated health data. The embodiment of analyzing the change degree of health data by comparing the recent health data with the accumulated health data will be described in more detail with reference to FIG. 5.

In operation S450, the server 1000 generates a response message including a first message regarding a health state and health data, a second message providing emotional consolation, and a third message proposing a follow-up action associated with the analyzed health data, by using an NLG. According to an embodiment, the first message may be generated based on the information of the user and the condition information according to the health state and the type of health data, such as the number of steps, a sleep duration, a heart rate, and an exercise amount. According to an embodiment, the second message may include text and a graphic image. The third message may include a message that proposes a follow-up action associated with at least one of the types of analyzed health data, for example, the number of steps, a sleep duration, a heart rate, and an exercise amount.

In operation S460, the server 1000 provides the generated response message to the device 2000. According to an embodiment, the server 1000 may transmit the response message to the device 2000 so that the response message may be output through the device 2000.

The device 2000 may display the response message received from the server 1000 on the display.

According to another embodiment, the device 2000 may output the response message in the form of an audio signal. In this case, the server 1000 may convert the response message into an audio signal by using a TTS model, and may transmit the audio signal to the device 2000. According to another embodiment, when the device 2000 includes a TTS model, even when the device 2000 receives a response message having a text form from the server 1000, the device 2000 may convert the received response message into an audio signal and may output the audio signal through a speaker.

Figure 5:
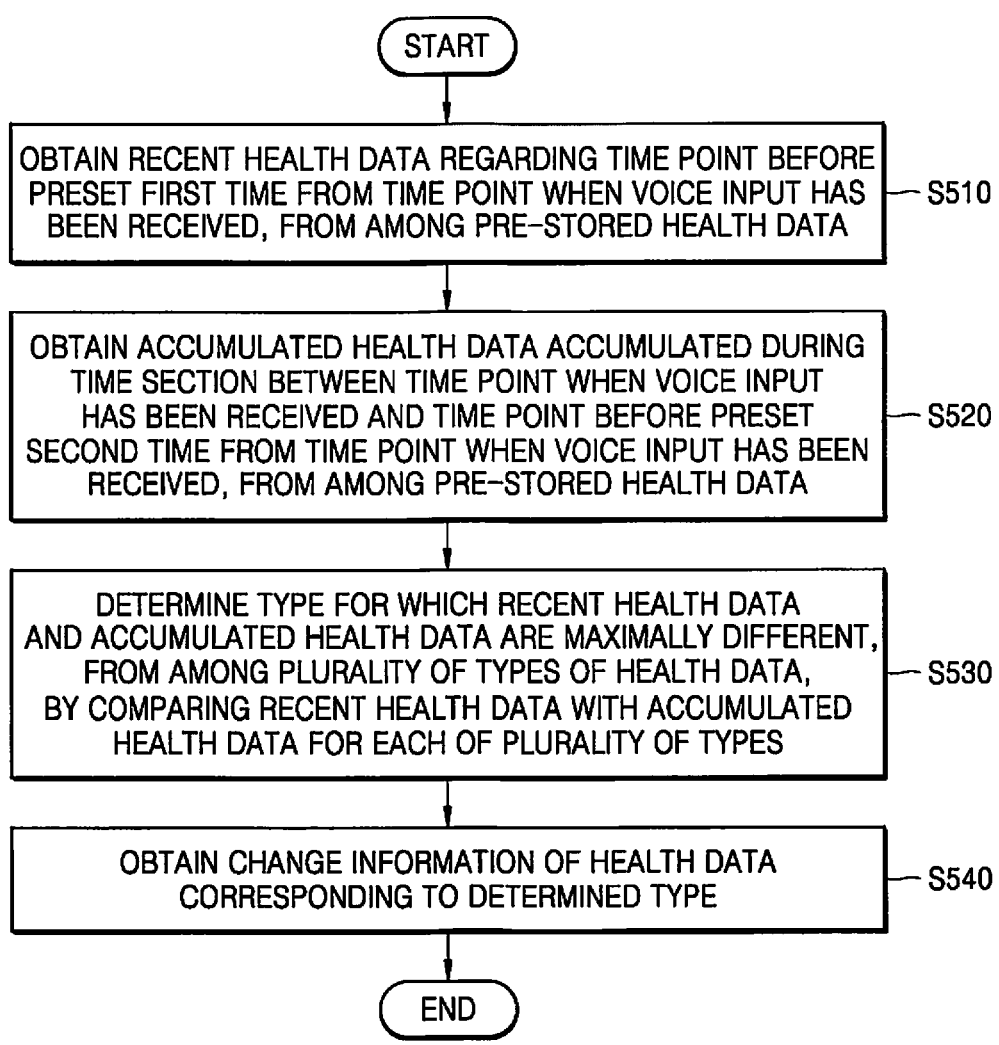
FIG. 5 is a flowchart of a method, performed by a server according to an embodiment of the present disclosure, of analyzing pre-stored health data.

FIG. 5 is a flowchart of a method, performed by the server 1000 according to an embodiment of the present disclosure, of analyzing pre-stored health data.

In operation S510, the server 1000 obtains recent health data regarding a time point before a preset first time from a time point when the voice input has been received, from among pre-stored health data. According to an embodiment, the server 1000 may selectively obtain only health data before 24 hours from the time point when the voice input has been received from the device 2000, from among health data pre-stored in a storage 1400 of FIG. 16. For example, the server 1000 may selectively obtain only health data collected and stored for one day, namely, yesterday, from among the health data stored in the storage 1400.

In operation S520, the server 1000 obtains accumulated health data accumulated during a time section between the time point when the voice input has been received and a time point before a preset second time from the time point when the voice input has been received, from among the pre-stored health data. According to an embodiment, the server 1000 may selectively obtain only health data collected through the device 2000 during a time interval between the time point when the voice input has been received from the device 2000 and a time point before one week from the time point when the voice input has been received, namely, from one week before the time point when the voice input has been received to the time point when the voice input has been received, from among the health data pre-stored in the storage 1400.

The server 1000 may calculate an average value of health data during one week, and may obtain accumulated health data, based on the calculated average value. According to an embodiment, the server 1000 may calculate the average value for each type of health data during one week. For example, the server 1000 may calculate an average value for the number of steps during one week from the time point when the voice input has been received. As another example, the server 1000 may calculate an average value of a sleep duration obtained for one week from the time point when the voice input has been received.

In operation S530, the server 1000 determines a type of health data for which the recent health data and the accumulated health data differ the most, from among a plurality of types of health data, by comparing the recent health data and the accumulated health data for each of the plurality of types with each other. According to an embodiment, the server 1000 may calculate a difference between the recent health data and the accumulated health data for each of the plurality of types, and may determine a type for which the calculated difference is maximum from among the plurality of types.

According to an embodiment, the server 1000 may calculate a changing rate of the health data by dividing the differences calculated for the plurality of types of the health data by the respective accumulated health data of the plurality of types. In this case, the server 1000 may determine a type for which the calculated changing rate is maximum.

In operation S540, the server 1000 obtains change information of the health data corresponding to the determined type. According to an embodiment, the server 1000 may determine whether the recent health data of the determined type has increased or decreased compared with the accumulated health data. For example, when the type for which a difference of the health data is maximum determined in operation S530 is the number of steps, the server 1000 may determine whether the number of recent steps, namely, the number of steps taken yesterday, has increased or decreased compared with an accumulated number of steps, namely, an average of the number of steps during one week.

Figure 6:
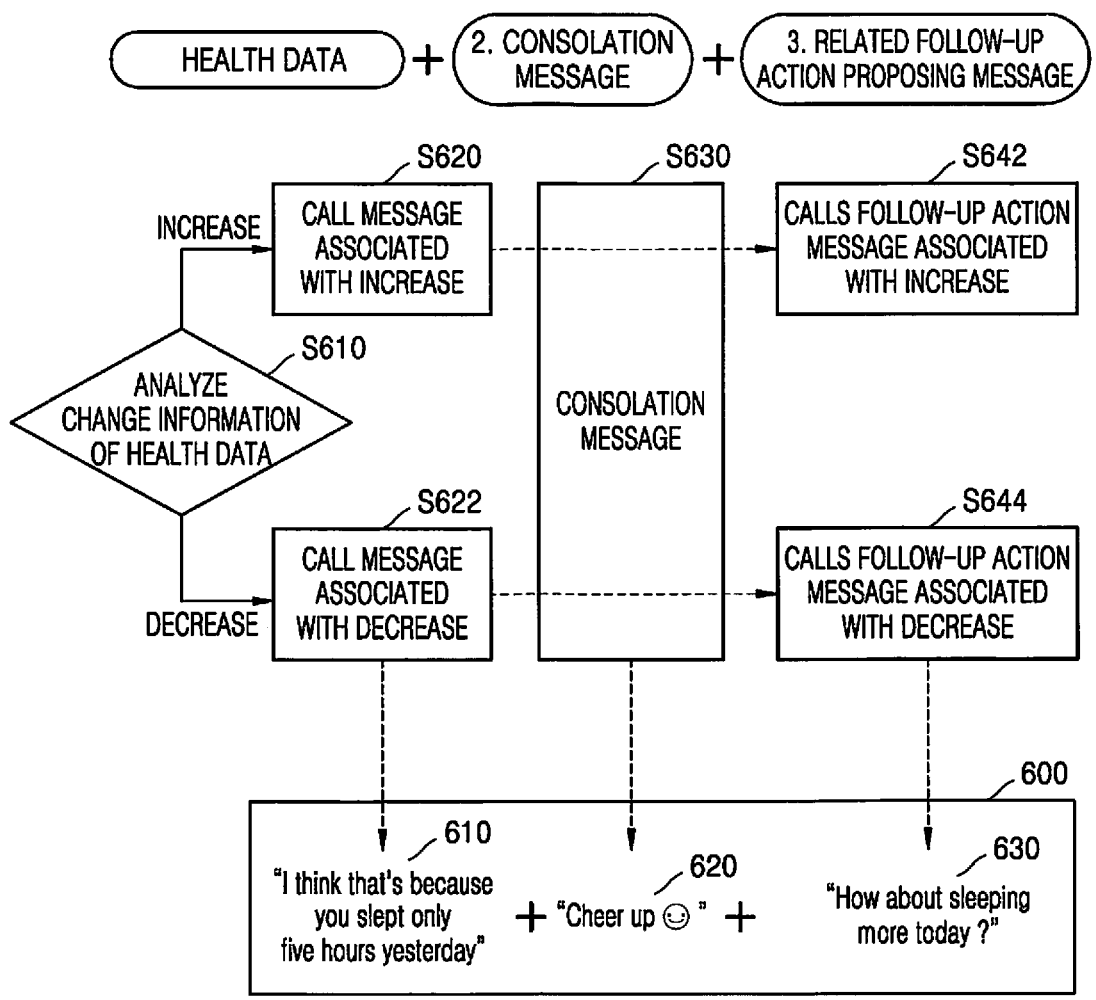
FIG. 6 is a flowchart of a method, performed by a server according to an embodiment of the present disclosure, of generating a response message.

FIG. 6 is a flowchart of a method, performed by the server 1000 according to an embodiment of the present disclosure, of generating a response message. FIG. 6 illustrates operations performed by the server 1000 after operation S540 of FIG. 5.

In operation S610, the server 1000 analyzes the change information of the health data. According to an embodiment, the server 1000 may determine whether the recent health data corresponding to the type determined in operation S530 of FIG. 5 has increased or decreased compared with the accumulated health data.

When the recent health data has increased compared with the accumulated health data, the server 1000 calls a message associated with an increase (S620). According to an embodiment, the server 1000 may call a message associated with an increase of the health data corresponding to the determined type, from among pre-stored health state messages.

When the recent health data has decreased compared with the accumulated health data, the server 1000 calls a message associated with a decrease (S622). According to an embodiment, the server 1000 may call a message associated with a decrease of the health data corresponding to the determined type, from among the pre-stored health state messages. For example, when a sleep duration collected yesterday is 5 hours and a sleep duration average during one week is 6 hours, recent health data for a sleep duration has decreased compared with the accumulated health data, and the server 1000 may call a health state message 610 such as "I think that's because you slept only five hours yesterday" from among the pre-stored health state messages.

In operation S630, the server 1000 selectively extracts a specific consolation message from among pre-stored consolation messages. According to an embodiment, the server 1000 may randomly select the specific consolation message from among the pre-stored consolation messages. For example, the server 1000 may extract a consolation message 620 such as "Cheer up".

When the recent health data has increased compared with the accumulated health data, the server 1000 calls a follow-up action message associated with an increase from among pre-stored follow-up action messages (S642). When the recent health data has decreased compared with the accumulated health data, the server 1000 may call a follow-up action message associated with a decrease from among the pre-stored follow-up action messages (S644). According to an embodiment, the server 1000 may call a follow-up action message corresponding to the determined type. For example, the server 1000 may call a follow-up action message 630 such as "How about sleeping more today?", from among the pre-stored follow-up action messages.

The server 1000 according to an embodiment of the present disclosure may generate a response message 600 including the health state message 610 associated with a change in the health data, the consolation message 620 providing emotional consolation to the user, and the follow-up action message 630 proposing a follow-up action associated with the health state of the user. For example, the health state message 610 may be generated based on a result of analyzing a change in the health data about the sleep duration of the user, such as 'I think that's because you slept only five hours yesterday'. The consolation message 620 may be generated by being arbitrarily selected from the consolation messages pre-stored in the server 1000, such as, 'Cheer up'. The follow-up action message 630 may be a message that proposes a follow-up action of having a more sleep duration according to the health state of the user, namely, a sleeping failure for a certain period of time yesterday, such as 'How about sleeping more today?'.

Figure 7A:
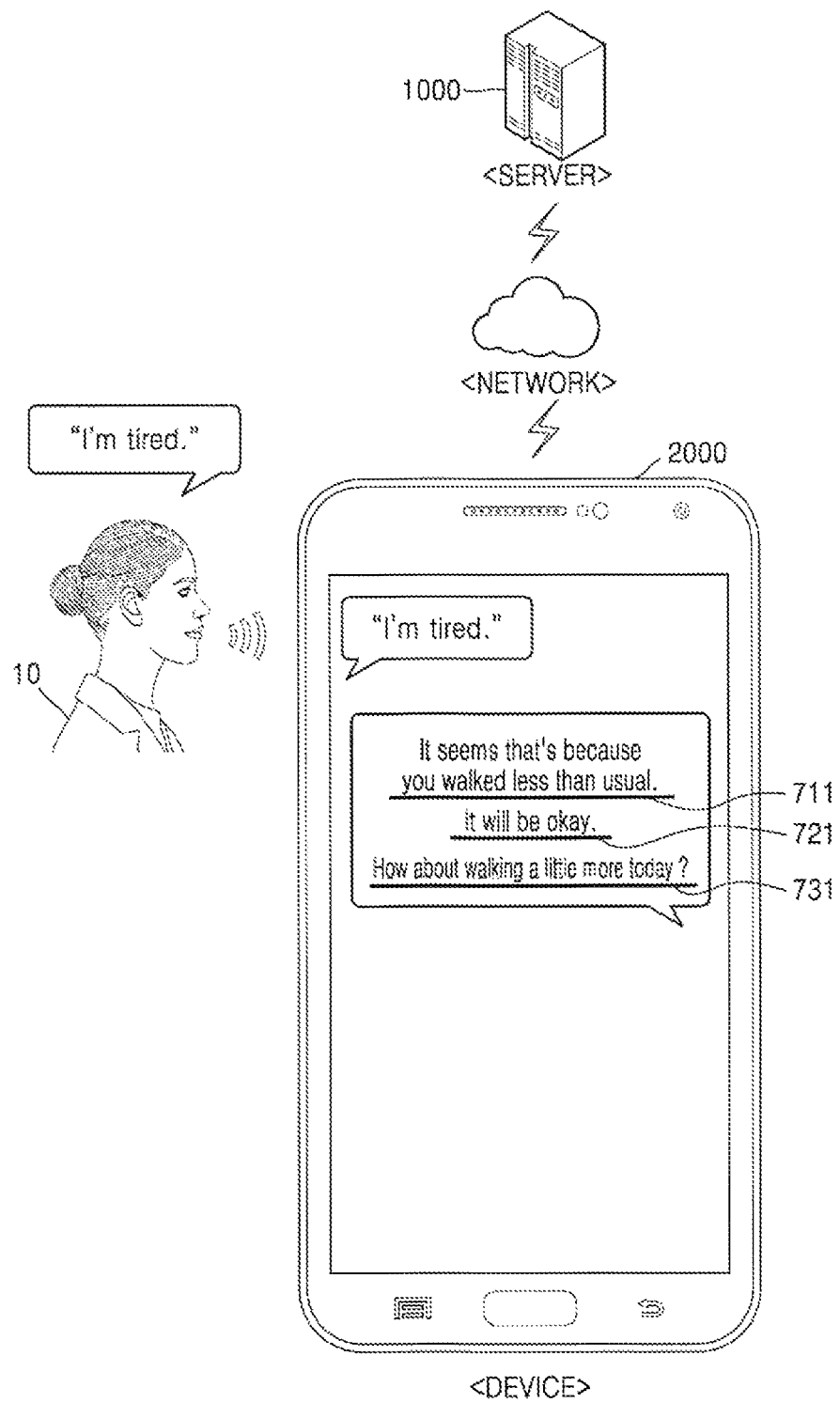
FIGS. 7A through 7C are views illustrating examples in which a device according to an embodiment of the present disclosure outputs response messages received from a server.
Figure 7B:
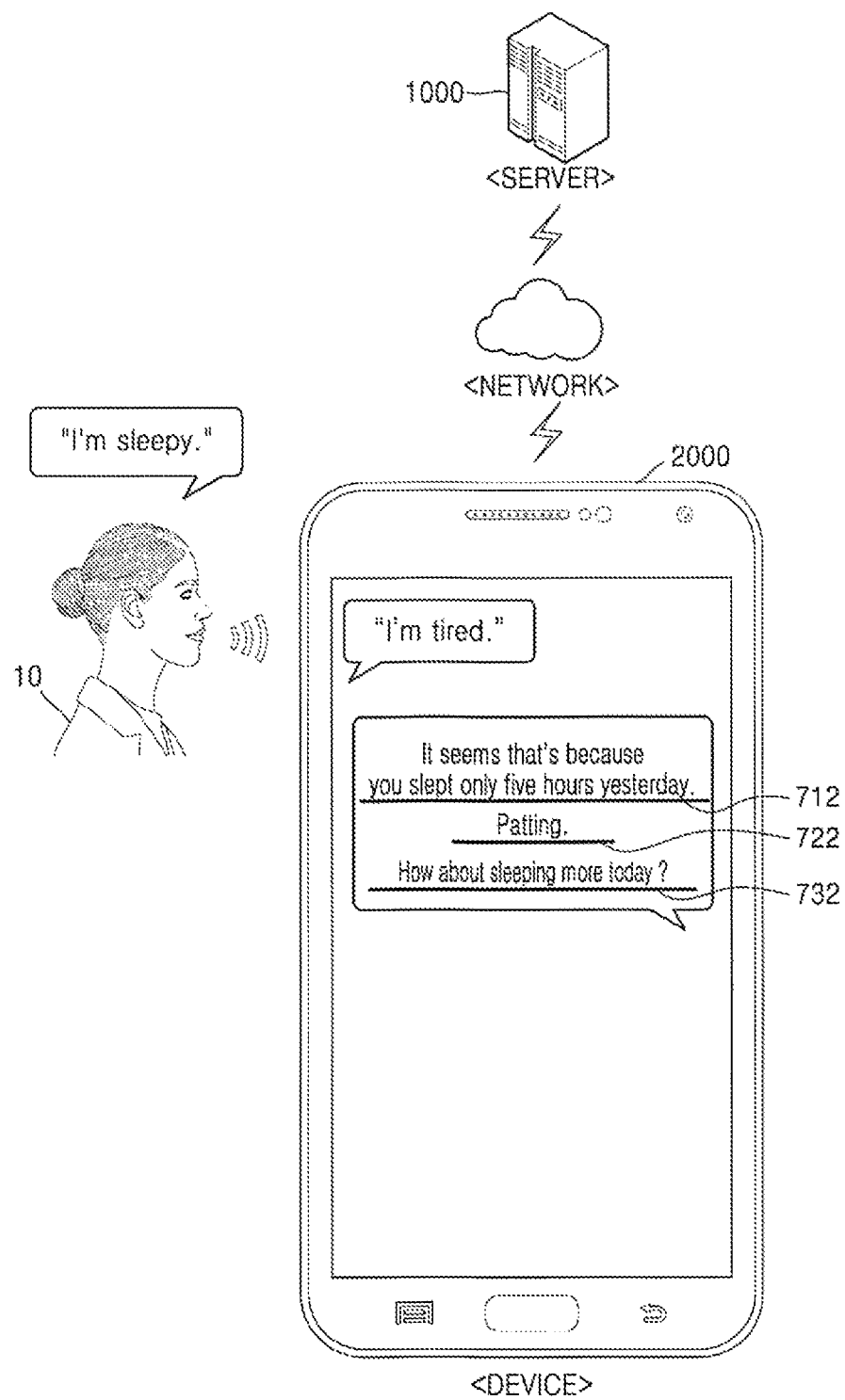
Figure 7C:
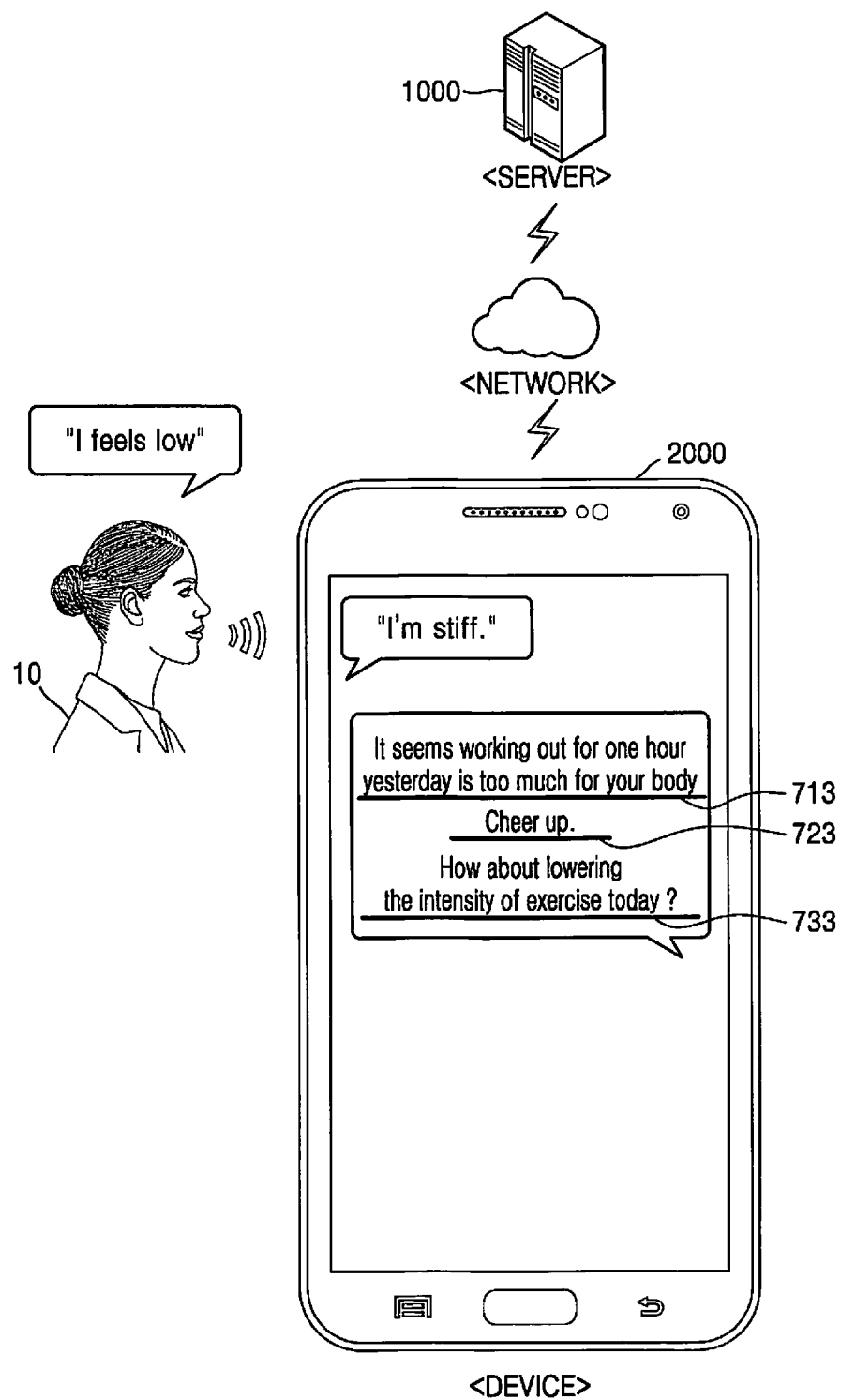

FIGS. 7A through 7C are views illustrating examples in which the device 2000 according to an embodiment of the present disclosure outputs response messages.

Referring to FIG. 7A, when obtaining a voice input including state information such as 'I'm tired' from the server 1000, the device 2000 may display a response message including a first message 711 generated based on health data pre-stored in the server 1000, a second message 721 as a consolation message providing emotional consolation to the user 10, and a third message 731 proposing a follow-up action associated with health data. The response message may be generated by the server 1000, and the device 2000 may obtain the response message from the server 1000.

According to an embodiment, the device 2000 may display a response message on a display. However, embodiments are not limited thereto. According to an embodiment, the device 2000 may output the response message in the form of an audio signal through the audio output interface 2220 of FIG. 17.

As shown in FIG. 7A, the server 1000 may generate the first message 711 such as 'It seems that's because you walked less than usual', based on a result of analyzing information of a change in the number of steps taken by the user before a preset time period from the time point when the voice input is received by the device 2000, compared with the number of steps usually taken by the user. The server 1000 may generate the second message 721 as a consolation message, such as 'It will be okay'. The server 1000 may generate the third message 731 including a proposal that induces a follow-up action of increasing the number of steps, based on the change degree of the number of steps taken by the user, namely, a decrease in the number of steps, such as 'How about walking a little more today?'.

As shown in FIG. 7B, the device 2000 may display a response message including a first message 712 associated with a sleep duration of the user, such as 'It seems that's because you slept only five hours yesterday', a second message 722 as is a consolation message such as 'Patting', and a third message 732 including a proposal that induces a follow-up action of increasing the sleep duration according to a decrease in the sleep duration, such as 'How about sleeping more today?'. The response message may be generated by the server 1000, and the device 2000 may obtain the response message from the server 1000.

When a voice input of the user 10 associated with a sleep duration, such as 'I'm sleepy', is input through the device 2000, the server 1000 may ascertain the degree of a change in the sleep duration of the user within a preset duration from the time point when the voice input has been received compared with an average sleep duration, by analyzing pre-stored health data about a sleep duration. The server 1000 may generate the first message 712, based on the ascertained increase or decrease in the sleep duration. The server 1000 may generate the second message 722 by randomly selecting and calling a consolation message such as 'Patting' from among pre-stored consolation messages. The server 1000 may generate the third message 732 including a proposal that induces a follow-up action of increasing the sleep duration, based on the change degree of the sleep duration of the user, namely, a decrease in the sleep duration, such as 'How about sleeping more today?'.

Referring to FIG. 7C, when receiving a voice input including state information such as 'I feel low' from the user 10, the device 2000 may display a response message including a first message 713 generated based on a change in health data, such as 'It seems working out for one hour yesterday is too much for your body', a second message 723 as a consolation message providing emotional consolation to the user 10, and a third message 733 proposing a follow-up action associated with the change in the health data. The response message may be generated by the server 1000, and the device 2000 may obtain the response message from the server 1000.

As shown in FIG. 7C, the server 1000 may generate the first message 713 such as 'It seems working out for one hour yesterday is too much for your body', based on a result of analyzing a current health state of the user, based on health data. The server 1000 may generate the second message 723 as a consolation message, such as, 'Cheer up'. The server 1000 may generate the second message 723 by randomly selecting and calling a consolation message such as 'Cheer up' from among pre-stored consolation messages. The server 1000 may generate the third message 733 including a proposal that induces a follow-up action of decreasing an exercise duration or exercise intensity of the user, such as 'How about decreasing the exercise intensity a little today?'.

FIG. 8 is a view illustrating an example in which the device 2000 according to an embodiment of the present disclosure outputs a response message 810, based on event information of a user.

Referring to FIG. 8, the device 2000 may display, on the display 2210, the response message 810 generated based on a voice input from the user 10. According to an embodiment, the device 2000 may output the response message 810 having an audio signal form through the audio output interface 2220 of FIG. 17.

The device 2000 may transmit the voice input obtained from the user 10 to the server 1000. The server 1000 may receive the voice input from the device 2000, and may convert the voice input into text through ASR. The server 1000 may recognize information related to event registration or event inquiry from the text by interpreting the text by using the NLU model. The server 1000 may generate the response message 810, based on the recognized event information of the user. According to an embodiment, the server 1000 may generate the response message 810 by using an NLG According to an embodiment, the server 1000 may generate the response message 810 including a first message 820 generated by calculating a frequency of an event and a second message 830 representing an emotional reaction to the type of event, and may provide the generated response message 810 to the device 2000.

As shown in FIG. 8, when receiving, from the user 10, a voice input of registering a travel event such as 'Register a Hawaii trip from August 12th to August 17th', the device 2000 may transmit the voice input to the server 1000, and the server 1000 may generate the first message 820 by calculating a frequency of "a travel event" of 'Second trip in this year'. The server 1000 may generate the second message 830 representing an emotional reaction to the travel event, such as 'Exciting'.

A conversation type that users frequently perform through the server 1000 including an interactive artificial assistant module using AI is a request regarding execution of a function. For example, there are many dialogs instructing the device 2000 to perform a specific function, such as 'Register schedules', 'Inform me of the weather', and 'Set the alarm'. A server 1000 including a conventional interactive artificial assistant generates a dry response message such as 'Registration is completed', 'Transmission has been done', or 'Setting has been done' and transmits the dry response message to the device 2000, and thus users may not feel emotional intimacy with the device 2000 but may feel as if they are talking with a machine.

The server 1000 according to an embodiment of the present disclosure may increase intimacy with a user by generating a response message including a first message 820 generated based on at least one of the event type of the user, an execution frequency according to the event type, and schedule calculation in correspondence with a voice input of the user of instructing to perform a specific function, for example, a function of registering event information or inquiring a schedule, and a second message 830 providing an emotional reaction to the event to the user, and providing the generated response message to the device 2000 so that the generated response message is output through the device 2000.

Figure 9:
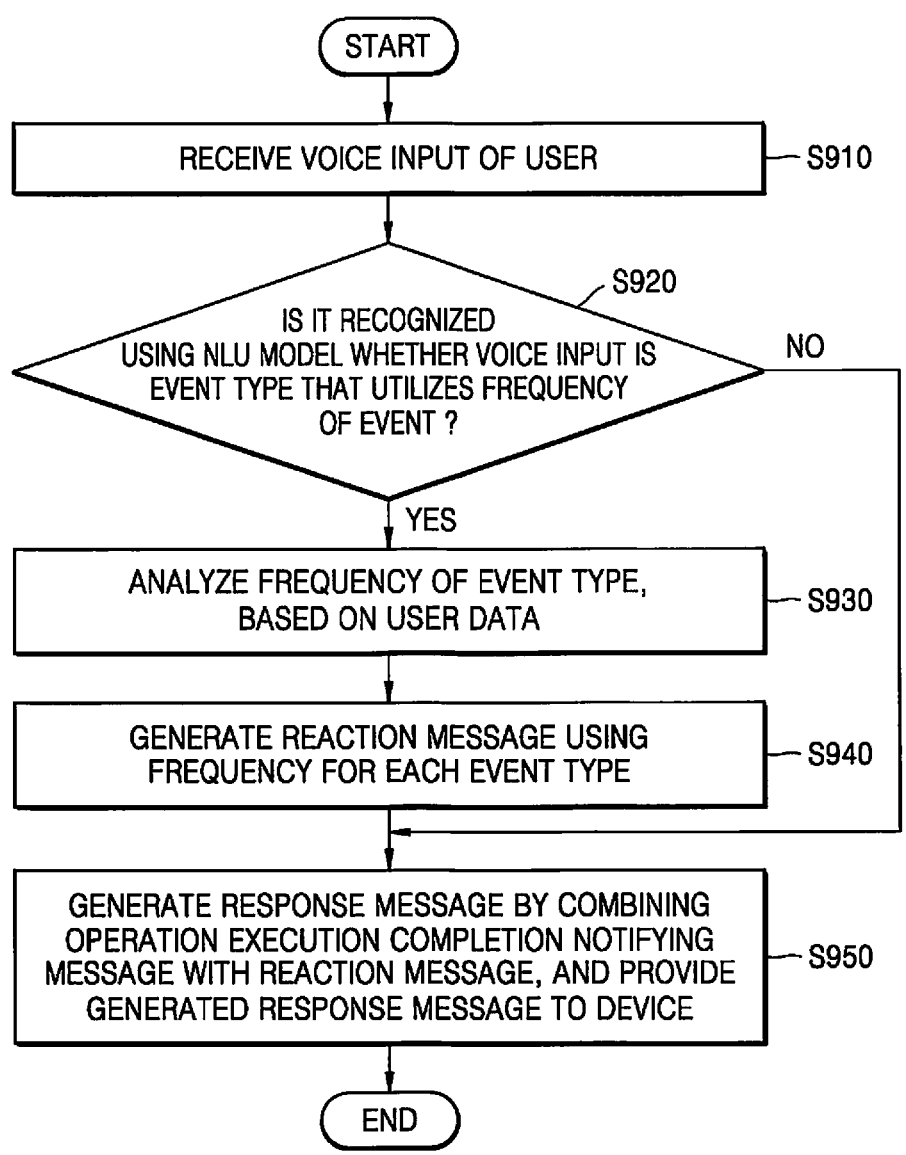
FIG. 9 is a flowchart of a method, performed by a server according to an embodiment of the present disclosure, of providing a response message, based on event information of a user.

FIG. 9 is a flowchart of a method, performed by the server 1000 according to an embodiment of the present disclosure, of providing a response message, based on event information of a user.

In operation S910, the server 1000 receives a voice input of the user from the device 2000. According to an embodiment, the voice input may include an instruction regrading function execution including at least one of event registration, event inquiry, and schedule inquiry.

The voice input received from the device 2000 may be an utterance of instructing execution of a function of registering or inquiring an event schedule, such as 'Register a Sydney trip', 'When is my birthday?', or 'Inform me of a first schedule on August'.

In operation S920, the server 1000 recognizes whether the voice input is an event type that utilizes a frequency of an event, by using an NLU model. According to an embodiment, the server 1000 may convert the voice input into text by performing ASR by using an ASR model. According to an embodiment, the server 1000 may perform an ASR operation of converting a voice input into computer-readable text by using a predefined model such as an acoustic model (AM) or a language model (LM).

According to an embodiment, the server 1000 may recognize whether the content of the text is an event type that utilizes a frequency of an event, by interpreting the text by using the NLU model. The NLU model may be a model trained to determine whether the text includes information about the frequency of the event, by interpreting the text. According to an embodiment, the server 1000 may parse the text in units of morphemes, words, or phrases by using the NLU model, and may infer the meaning of a word extracted from the parsed text by using linguistic characteristics (e.g., a syntactic element) of the parsed morpheme, word, or phrase. The server 1000 may determine an event type corresponding to the inferred meaning of the word by comparing the inferred meaning of the word with predefined event types provided by the NLU model.

When it is recognized in operation S920 that the text is an event type that utilizes a frequency of an event (Y), the server 1000 analyzes the frequency of the event type, based on user data, in operation S930.

In operation S940, the server 1000 generates a reaction message using a frequency for each event type. According to an embodiment, the server 1000 may generate the reaction message by using an NLG.

In operation S950, the server 1000 generates a response message by combining an operation execution completion notifying message with the reaction message, and provides the generated response message to the device 2000.

When it is recognized in operation S920 that the text is not an event type that utilizes a frequency of an event (N), the server 1000 may output a response message, in operation S950, without analyzing the frequency of the event type (S930) and generating the reaction message using the frequency for each event type (S940).

Figure 10:
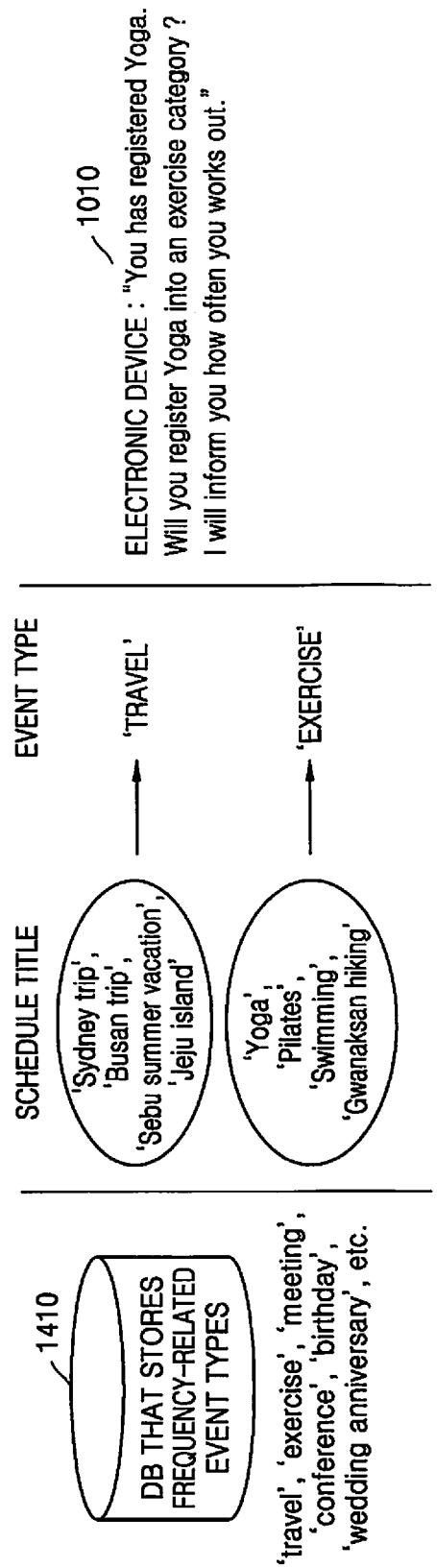
FIG. 10 is a view illustrating an example in which a server according to an embodiment of the present disclosure provides a response message according to a frequency-related event type.

FIG. 10 is a view illustrating an example in which the server 1000 according to an embodiment of the present disclosure generates a response message 1010 according to a frequency-related event type.

Referring to FIG. 10, the server 1000 may include a database (DB) 1410 storing frequency-related event types. The DB 1410 may be included in the storage 1400 of FIG. 16. The DB 1410 may store a frequency-related event including at least one of a travel, an exercise, a meeting, a conference, a birthday, and a wedding anniversary, for each type.

According to an embodiment, the DB 1410 may not be a component included in the server 1000, but may be configured as another server to which the server 1000 is connectable from the outside through a network or the like, the device 2000, or a cloud server.

The server 1000 may receive event information of the user, for example, a trip, a wedding anniversary, a birthday, an exercise, a meeting, and a conference, from the device 2000, and may store the received event information in the DB 1410. The server 1000 may store the received event information in the DB 1410, based on the frequency of the event type.

The server 1000 may previously define an event type that calculates a certain frequency, and may analyze the event type by analyzing the title of a registered event schedule or an inquired event schedule. The server 1000 may compare the pre-defined frequency-related event type with the analyzed event type.

According to an embodiment, the server 1000 may automatically classify a schedule recognized from the voice input received from the device 2000 into a certain event type. For example, 'Sydney trip', 'Busan trip', 'Sebu summer vacation', and 'Jeju island' may be classified into a travel event, and 'Yoga', 'Rates', 'Swimming', and 'Gwanaksan Mountain hiking' may be classified into an exercise event.

According to an embodiment, the server 1000 may inquire an event type to the user, or set a personalized event type based on a user input received through a setting menu. For example, the server 1000 may generate an inquiry message of inquiring the user about whether to register a specific event, namely, yoga, in an exercise category, such as 'You has registered Yoga. Will you register Yoga into an exercise category? I will inform you how often you works out.', and, in response to a user's response input indicating registration, may set a personalized event type by registering the event in an exercise event. According to an embodiment, the server 1000 may generate the inquiry message by using a NLG.

FIG. 11 is a table showing an example of a response message generated by the server 1000 according to an embodiment of the present disclosure, based on the types of events and the frequencies of the events.

The server 1000 may calculate the frequency of an event stored in the DB 1410 according to an event type 1110, and may generate a response message. The server 1000 may provide the generated response message to the device 2000, and the device 2000 may output the response message received from the server 1000. The event type 1110 may include, for example, at least one of a travel, a wedding anniversary, a birthday, an exercise, a meeting, and a conference.

The server 1000 may calculate a frequency of the type of each event, and a method of calculating the frequency may be set differently according to the type of event. The server 1000 may previously define a cycle of calculating the frequency for each event type, and a frequency item 1120 that is to be calculated. The frequency item 1120 is previously defined according to the type of event, and may include at least one of a travel frequency, a place frequency, a corresponding event frequency (e.g., wedding anniversary), an exercise frequency, a person/meeting encounter frequency, and a conference frequency.

The server 1000 may define the cycle of calculating the frequency and the frequency item that is to be calculated, by using a calendar application of the device 2000 or metadata of a photographed location stored in a memory in the device 2000 or in a cloud server. For example, when the event type 1110 is a travel, a frequency calculation cycle and method 1130 for a travel frequency may be calculating a sequential order of the travel during one year based on a registered date.

The server 1000 may generate a response message, based on information about the event type 1110 and the frequency item 1120 based on an event type. An exemplary response 1140 for the travel frequency, as an example of the response message, may be generated as 'This is the third trip in this year' or 'This is the last trip of 2018. Exciting AA. An exemplary response 1140 for the frequency of a wedding anniversary, as another example of the response message, may be generated as 'Today is the 10th wedding anniversaryr!'.

According to an embodiment, when there are a plurality of frequency calculation items for the same event type, the server 1000 may generate a response message according to priorities.

The server 1000 may correct frequency calculation according to the event type into a personalized frequency calculation algorithm through an inquiry or setting menu to the user. According to an embodiment, the server 1000 may generate a response message of 'I can see from the gallery that you have gone on a second trip to Daegwallyeong', as an accuracy improvement and personalization method 1150 in a frequency item for the travel event.

According to an embodiment, the server 1000 may generate an emotion-based reaction message according to an event type, or add an emotion-related emoticon to a generated reaction message.

According to an embodiment, the server 1000 may generate a response message for a follow-up action related to an event, and provide the generated response message to the device 2000. The device 2000 may output the response message received from the server 1000.

Figure 12A:
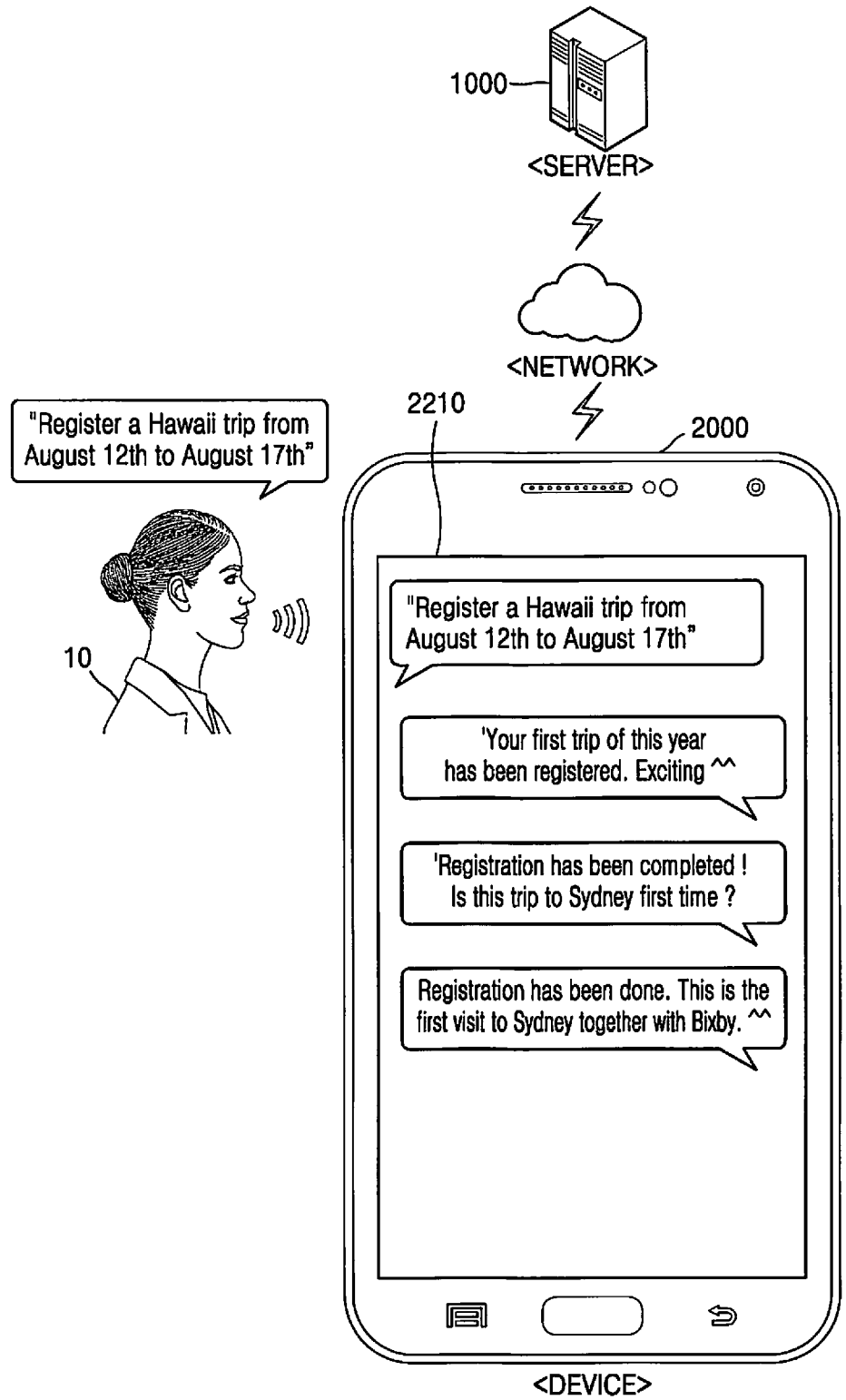
Figure 12B:
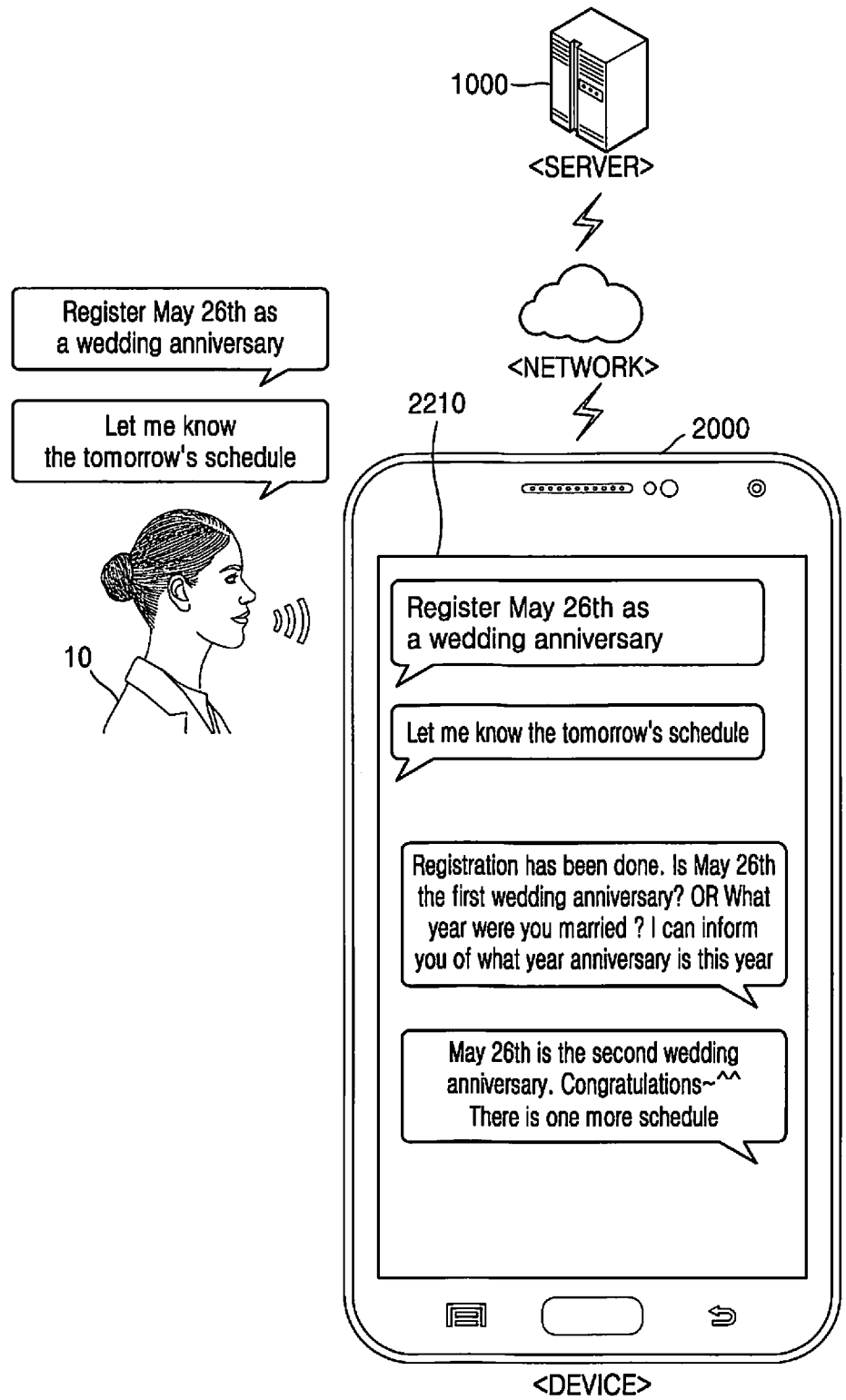

FIGS. 12A through 12C are views illustrating examples in which the device 2000 according to an embodiment of the present disclosure registers event information, based on an input utterance of a user, and outputs a response message, based on the registered event information.

In FIGS. 12A through 12C, the device 2000 may receive a voice input including a user's instruction of registering event information or a user's instruction of inquiring schedule information from the user, and may output a response message generated by calculating a frequency according to the type of event.

In FIGS. 12A through 12C, the device 2000 may transmit the voice input to the server 1000, and the server 1000 may generate the response message by calculating the frequency according to the type of event. According to an embodiment, the server 1000 may convert the voice input received from the device 2000 into text by performing ASR, and recognize the type of an event included in the text by interpreting the text by using an NLU model. The server 1000 may calculate the frequency according to the recognized event type, and may generate the response message, based on the calculated frequency. The server 1000 may transmit the generated replacement text to the device 2000.

In FIGS. 12A through 12C, the device 2000 may output a response message composed of a character, text, a GUI, or a combination thereof, on the display 2210.

However, embodiments are not limited thereto. According to another embodiment, the device 2000 may output the response message through the audio output interface 2220 of FIG. 17. In this case, the server 1000 may convert the response message having a text form into an audio signal by using a TTS model, and may transmit the audio signal to the device 2000. According to another embodiment, the device 2000 may include a TTS model. In this case, the device 2000 may convert the response message composed of the text received from the server 1000 into an audio signal by using the TTS model, and may output the audio signal to the audio output interface 2220 of FIG. 17.

As shown in FIG. 12A, when receiving a voice input of 'Register a Hawaii trip from August 15th to August 17th' from the user 10, the device 2000 may output a response message for the frequency of a travel event, such as 'Your first trip of this year has been registered. Exciting ‘^^’, and also output an emotional reaction message such as 'Exciting' together with the response message. According to another embodiment, the device 2000 may output a response message including an operation execution completion notifying message according to an instruction and an inquiry message of inquiring about event information as a method of improving the accuracy, like 'Registration has been completed ! Is this trip to Sydney first time?'. According to another embodiment, the device 2000 may output a response message such as 'Registration has been done. This is the first visit to Sydney together with Bixby.^^', the response message including an operation execution completion notifying message and a message that provides information about the frequency according to the event type.

As shown in FIG. 12B, when receiving a voice input of 'Register May 26th as a wedding anniversary' from the user 10, the device 2000 may output a response message such as 'Registration has been done. Is May 26th the first wedding anniversary?', the response message including an operation execution completion notifying message and a message that improves and personalizes the accuracy by inquiring the user 10 about whether May 26th is the first anniversary. According to another embodiment, the device 2000 may output a response message including only a message of improving and personalizing the accuracy by inquiring the user 10 about a marriage year, such as 'What year were you married? I can inform you of what year anniversary is this year.'

When a voice input including an instruction about a function of inquiring a schedule, such as 'Let me know the tomorrow's schedule', is received from the user 10, the device 2000 may output a response message such as 'May 26th is the second wedding anniversary. Congratulations~^^ There is one more schedule', the response message including a message that notifies operation execution completion, a reaction message that provides an emotional reaction to the user 10, and an additional schedule confirmation message.

As shown in FIG. 12C, when receiving a voice input of 'Register a Yoga schedule for tomorrow' from the user 10, the device 2000 may output a response message including information indicating a frequency for an event type (exercise), such as 'You have registered a second exercise of this week'.

According to another embodiment, when the device 2000 receives a voice input including an instruction of registering an additional schedule for the same event type, such as 'Register a Yoga schedule for the day after tomorrow', from the user 10, the device 2000 may output a response message such as 'The third exercise of this week has been registered. oo who tries to exercise consistently is cool!', the response message including a message including frequency information for the event type and a reaction message that provides an emotional reaction to the user.

Figure 13A:
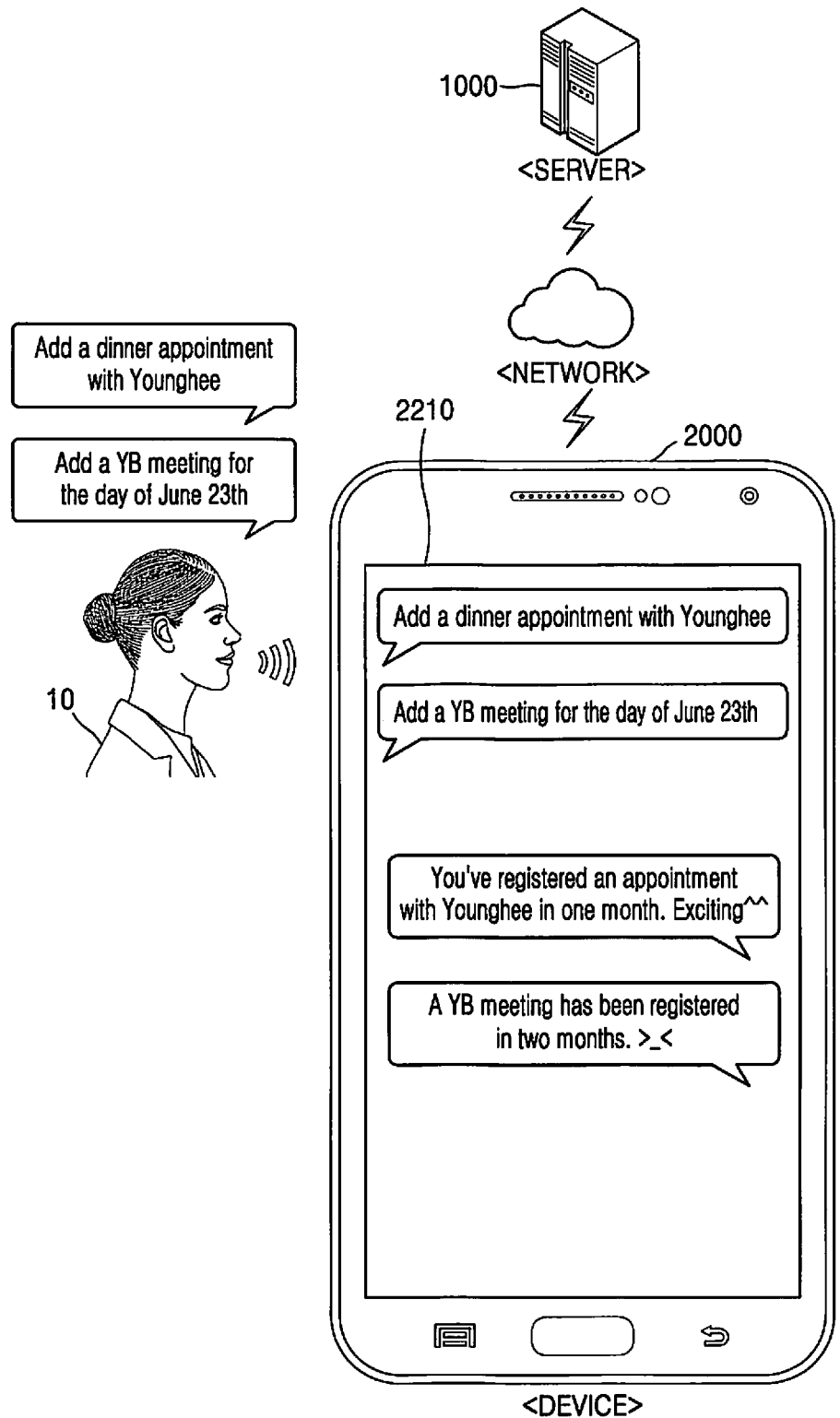
FIGS. 13A and 13B are views illustrating examples in which a device according to an embodiment of the present disclosure registers event information, based on a voice input of a user, and outputs a response message, based on the registered event information.
Figure 13B:
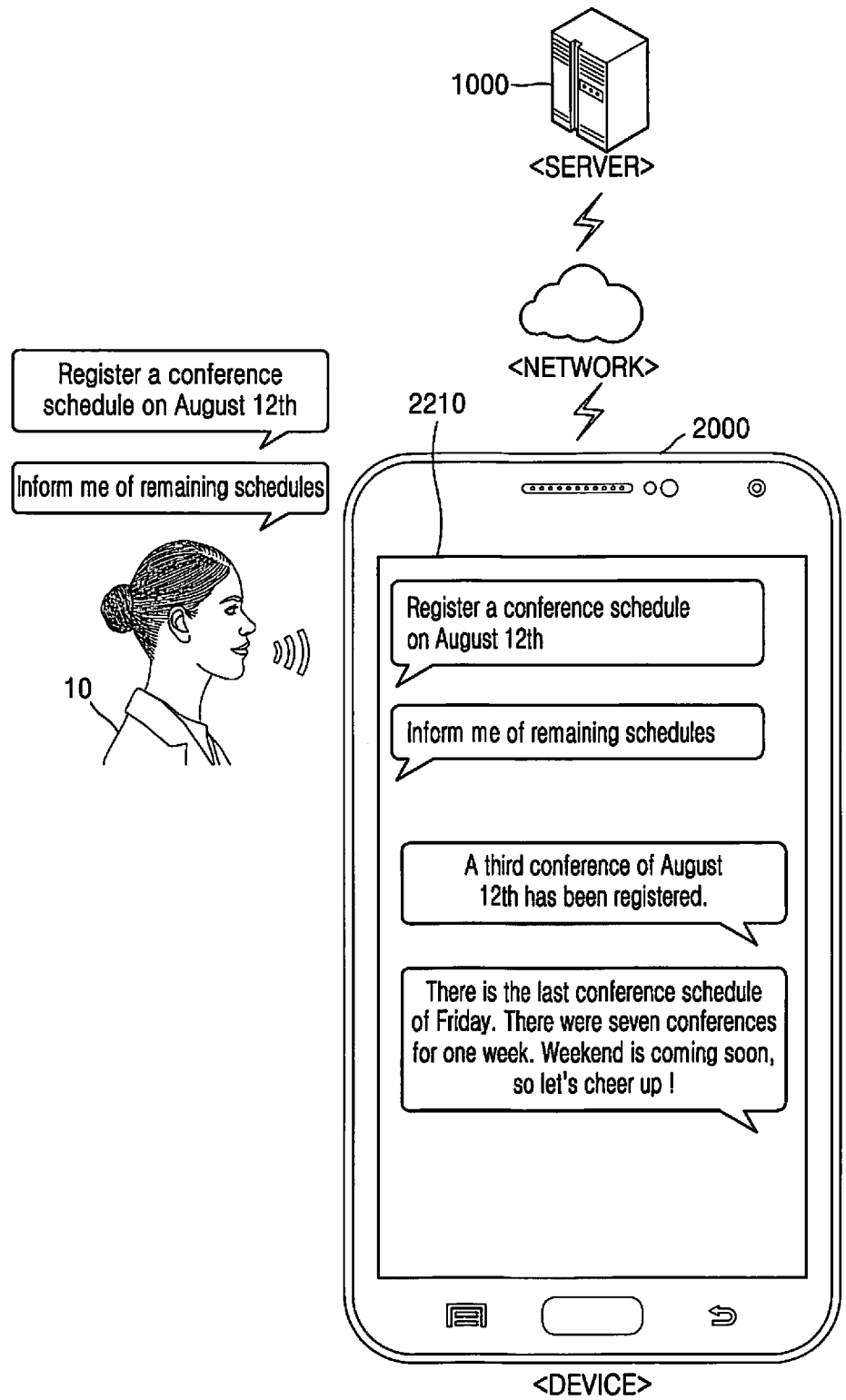

FIGS. 13A and 13B are views illustrating examples in which the device 2000 according to an embodiment of the present disclosure registers event information, based on a voice input of a user, and outputs a response message, based on the registered event information.

In FIGS. 13A and 13B, the device 2000 may output a response message composed of a character, text, a GUI, or a combination thereof, on the display 2210.

However, embodiments are not limited thereto. According to another embodiment, the device 2000 may output the response message through the audio output interface 2220 of FIG. 17. In this case, the server 1000 may convert the response message having a text form into an audio signal by using a TTS model, and may transmit the audio signal to the device 2000. According to another embodiment, the device 2000 may include a TTS model. In this case, the device 2000 may convert the response message composed of the text received from the server 1000 into an audio signal by using the TTS model, and may output the audio signal to the audio output interface 2220 of FIG. 17.

As shown in FIG. 13A, when receiving a voice input of 'Add a dinner appointment with Younghee' from the user 10, the device 2000 may calculate a time period from the moment when the voice input regarding the meeting event is received, and may output a response message such as 'You've registered an appointment with Younghee in one month. Exciting^^', the response message including a message for a frequency associated with the calculated time period and a reaction message providing an emotional reaction to the user 10.

According to another embodiment, when the device 2000 receives a voice input including an instruction of registering an additional schedule for the same event type (meeting), such as 'Add a YB meeting for the day of June 23th', from the user 10, the device 2000 may output a response message such as 'A YB meeting has been registered in two months. >_<', the response message including a message including frequency information for the event type and a reaction message (>_<) providing an emotional reaction to the user 10. The reaction message may include at least one of a special character, an emoticon, and a combination thereof.

As shown in FIG. 13B, when receiving a voice input of 'Register a conference schedule on August 12th' from the user 10, the device 2000 may output a response message including a message providing information about the frequency of an event type (conference) and an operation execution completion notifying message, such as 'A third conference of August 12th has been registered'.

According to another embodiment, when the device 2000 receives from the user 10 a voice input including an instruction of inquiring a schedule, such as 'Inform me of remaining schedules', the device 2000 may output a response message such as 'There is the last conference schedule of Friday. There were seven conferences for one week. Weekend is coming soon, so let's cheer up!', the response message including a message that provides information about the frequency of an event type (conference) before a preset time period from the moment when the voice input has been received, and a message that provides an emotional reaction to the user 10.

Figure 14:
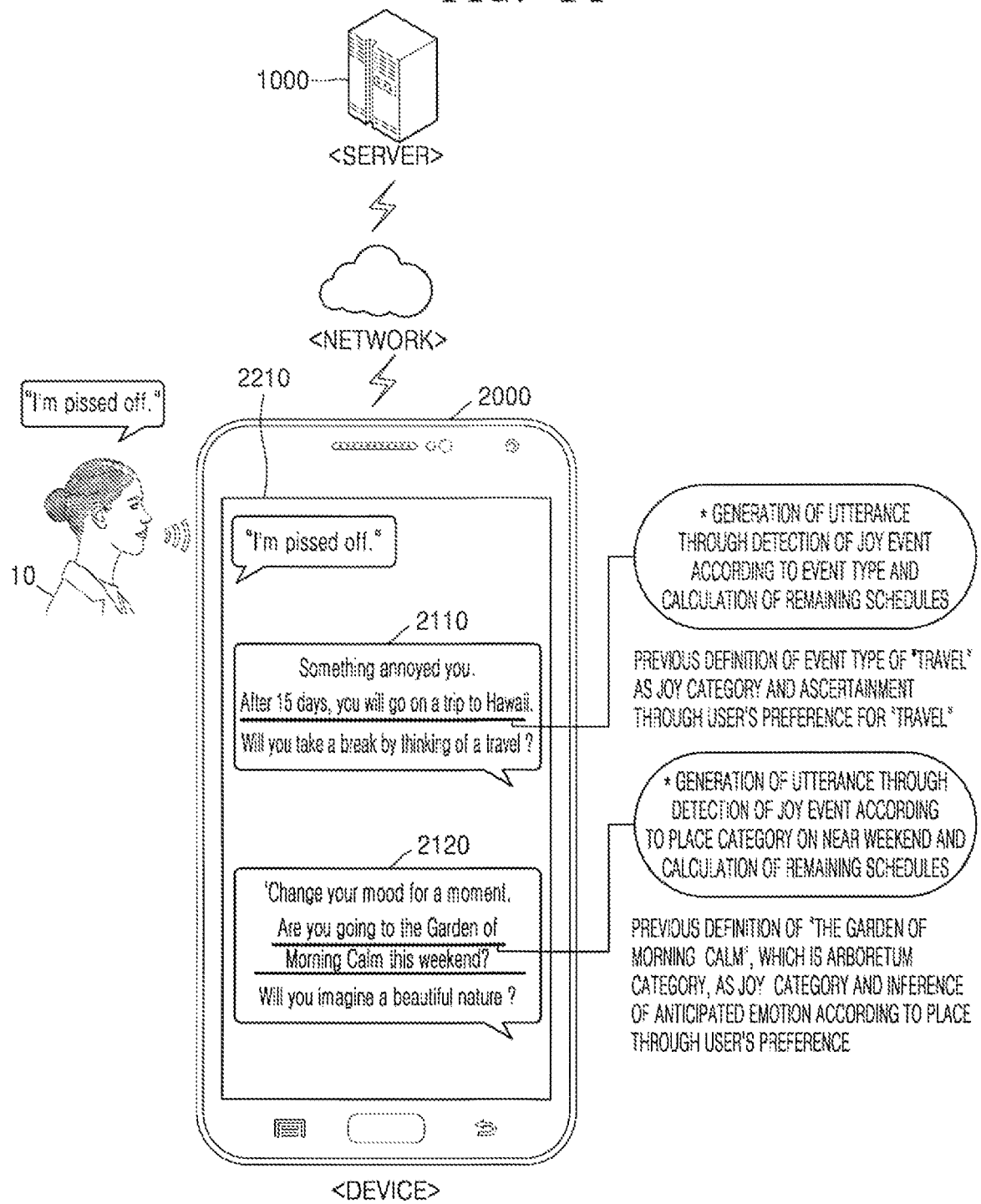
FIG. 14 is a view illustrating an example in which a device according to an embodiment of the disclosure outputs a response message, based on a joyful event detected from a voice input of a user.

FIG. 14 is a view illustrating an example in which the device 2000 according to an embodiment of the present disclosure detects a joy event according to an event type included in a voice input received from a user and outputs a response message, based on the detected joy event.

Referring to FIG. 14, when the device 2000 receives from the user 10 a voice input of expressing a negative emotion, the server 1000 may analyze whether there is an event corresponding to a joy category among the schedules within a preset time period from the moment when the voice input is received, may generate a response message by using a time period remaining until a schedule of the event corresponding to the joy category, and may transmit the response message to the device 2000. According to an embodiment, the device 2000 may transmit the voice input received from the user 10 to the server 1000, and the server 1000 may convert the voice input into text by performing ASR and may recognize whether the text includes a negative emotion, by using an NLU model. The server 10 may analyze whether there is an event corresponding to a joy category among the schedules within a preset time period from the moment when the voice input is received from the user 10, and may generate a response message by using a time period remaining until a schedule of the event corresponding to the joy category. The server 1000 may transmit the generated replacement text to the device 2000.

The device 2000 may output the response message received from the server 1000. According to an embodiment, the device 2000 may output a response message composed of a character, text, a GUI, or a combination thereof, on the display 2210.

However, embodiments are not limited thereto. According to another embodiment, the device 2000 may output the response message through the audio output interface 2220 of FIG. 17. In this case, the server 1000 may convert the response message having a text form into an audio signal by using a TTS model, and may transmit the audio signal to the device 2000. According to another embodiment, the device 2000 may include a TTS model. In this case, the device 2000 may convert the response message composed of the text received from the server 1000 into an audio signal by using the TTS model, and may output the audio signal to the audio output interface 2220 of FIG. 17.

For example, when receiving from the user 10 a voice input of expressing a negative emotion, such as 'I'm pissed off', the device 2000 may output a response message 2110 such as 'Something annoyed you. After 15 days, you will go on a trip to Hawaii. Will you take a break by thinking of a travel?', by detecting a joy event according to an event type and calculating schedules remaining from the moment when the voice input is received to the joy event. The server 1000 may previously define an event type of "travel" as a joy category. The server 1000 may recognize whether a travel is included in the joy category, based on user's preference for "travel".

According to another embodiment, in response to the voice input of the user 10 expressing a negative emotion, the device 2000 may output a response message 2120 such as 'Change your mood for a moment. Are you going to the Garden of Morning Calm this weekend? Will you imagine a beautiful nature?', by detecting a joy event according to a place category from then schedules (coming weekend) within a preset time period from the moment when the input is uttered and calculating schedules remaining from the moment when the input is uttered to the joy event. The server 1000 may previously define "the Garden of Morning Calm", which is an arboretum category, as a joy category. According to an embodiment, the server 1000 may infer an anticipated emotion according to a place, based on the user's preference, generate the response message 2120 by using the inferred anticipated emotion, and transmit the generated response message 2120 to the device 2000. The device 2000 may output the response message 2120 received from the server 1000.

Figure 15:
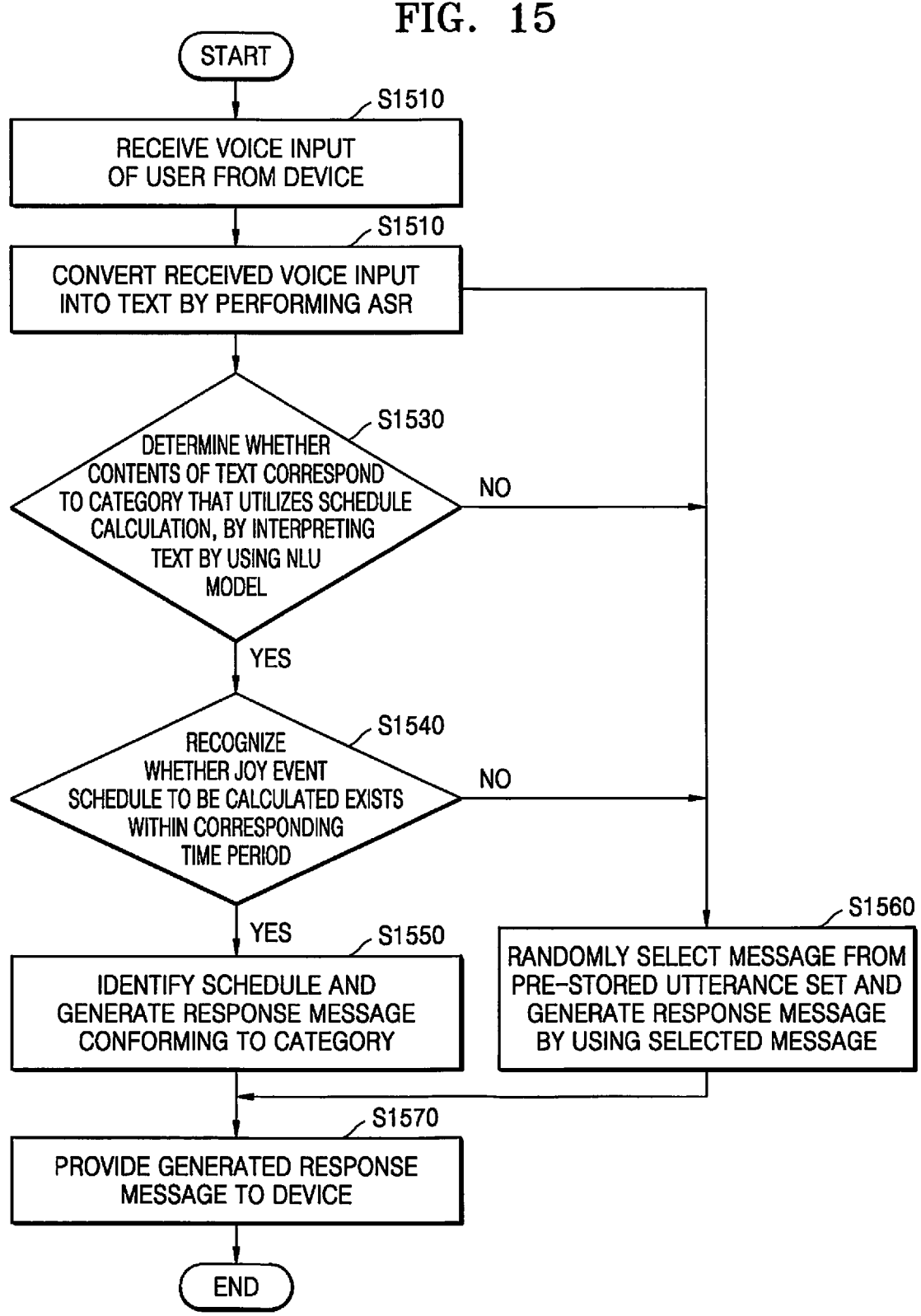
FIG. 15 is a flowchart of a method, performed by a server according to an embodiment of the present disclosure, of detecting a joyful event according to an event type of a user and providing a response message, based on the detected joyful event.

FIG. 15 is a flowchart of a method, performed by the server 1000 according to an embodiment of the present disclosure, of detecting a joy event according to an event type of a user and providing a response message, based on the detected joy event.

In operation S1510, the server 1000 receives a voice input of the user from the device 2000. According to an embodiment, the device 2000 may receive a voice input including uttered contents representing a negative state of the user or an emotion that needs diversion. The device 2000 may transmit the voice input received from the user to the server 2000.

According to an embodiment, the server 1000 may receive, from the device 2000, device ID information of the device 2000 (e.g., device ID) and account information of a user who uses the device 2000 (e.g., user ID).

In operation S1520, the server 1000 converts the received voice input into text by performing ASR. According to an embodiment, the server 1000 may perform an ASR operation of converting a voice input into computer-readable text by using a predefined model such as an acoustic model (AM) or a language model (LM). When the server 1000 receives a sound signal from which noise has not been removed from the device 2000, the server 1000 may obtain an audio signal by removing noise from the received sound signal, and may perform ASR on the audio signal.

In operation S1530, the server 1000 determines whether the contents of the text correspond to a category that utilizes schedule calculation, by interpreting the text by using an NLU model. According to an embodiment, the server 1000 may previously define an event type that calculates a certain frequency. The server 1000 may parse the text into which the voice input of the user is converted, in units of morphemes, words, or phrases by using the NLU model, and may infer the meaning of a word extracted from the parsed text by using linguistic characteristics (e.g., a syntactic element) of the parsed morpheme, word, or phrase. The server 1000 may infer the contents about event information from among the words included in the text. The server 1000 may determine whether the contents of the text correspond to the category that utilizes schedule calculation, by comparing the inferred event information with the pre-defined event type.

When the contents of the text correspond to the category that utilizes schedule calculation (Y), the server 1000 recognizes whether a joy event schedule to be calculated exists within a corresponding time period, in operation S1540. The joy event may refer to a pleasant event capable of offsetting a negative emotion of a user within a preset time period from the moment when a voice input of the user is received.

When a joy event schedule exists within the preset time period from the moment when the voice input of the user is received (Y), the server 1000 identify a schedule and generates a response message conforming to the category, in operation S1550. According to an embodiment, the response message may include a joy event information providing message and an emotional reaction message.

In operation S1570, the server 1000 provides the generated response message to the device 2000.

When it is determined in operation S1530 that the text includes no event information corresponding to the category that utilizes schedule calculation (N), the server 1000 randomly selects a message from a pre-stored utterance set and generates a response message by using the selected message, in operation S1560.

Also, when it is recognized in operation S1540 that there are no calculated joy event schedules within the corresponding time period (N), the server 1000 randomly selects a message from the pre-stored utterance set and generates a response message by using the selected message, in operation S1560. In this case, the server 1000 provides the response message generated due to random selection from the pre-stored utterance set to the device 2000, in operation S1570.

FIG. 16 is a block diagram of structures of the server 1000 and the device 2000 according to an embodiment of the present disclosure.

Referring to FIG. 16, the device 2000 may include the display 2210, a processor 2300, a communication interface 2500, a microphone 2620, and a memory 2700. The components of FIG. 16 are only essential components for an operation of the device 2000, and the device 2000 may further include components other than the components of FIG. 16.

The device 2000 may receive a voice input (e.g., utterance) from a user through the microphone 2620, and may obtain an audio signal from the received voice input. The device 2000 may control the communication interface 2500 through the processor 2300, and may transmit the audio signal to the server 1000 through the communication interface 2500. According to an embodiment, the processor 2300 of the device 2000 may convert sound received through the microphone 2620 into a sound signal, and obtain an audio signal by removing noise (for example, a non-audio component) from the sound signal.

The memory 2700 may previously store ID information of the device 2000 (for example, ID information of a device) or account information of the user (for example, ID information of the user). According to an embodiment, when the device 2000 transmits the audio signal to the server 1000 through the communication interface 2500 under the control of the processor 2300, the device 2000 may transmit the ID information of the device 2000 (for example, ID information of a device) or account information of the user (for example, ID information of the user) stored in the memory 2700 to the server 1000.

The components of the device 2000 will be described later in more detail with reference to FIG. 17.

The server 1000 may include a communication interface 1100, a processor 1200, a memory 1300, and a storage 1400.

The communication interface 1100 may perform data communication with the device 2000 under the control of the processor 1200. The communication interface 1100 may perform data communication with the device 2000 by using at least one of data communication methods including, for example, a wired LAN, a wireless LAN, Wi-Fi, Bluetooth, Zigbee, Wi-Fi Direct (WFD), infrared Data Association (IrDA), Bluetooth Low Energy (BLE), near field communication (NFC), wireless broadband Internet (Wibro), World Interoperability for Microwave Access (WiMAX), a shared wireless access protocol (SWAP), wireless gigabit alliance (WiGig), and RF communication.

The processor 1200 may execute one or more instructions of a program stored in the memory 1300. The processor 1200 may be configured with a hardware component that performs arithmetic, logic, and input/output operations and signal processing. The processor 1200 may include, but is not limited to, at least one of, for example, a central processing unit, a microprocessor, a graphic processing unit, application specific integrated circuits (ASICs), digital signal processors (DSPs), digital signal processing devices (DSPDs), programmable logic devices (PLDs), and field programmable gate arrays (FPGAs).

The memory 1300 may include, for example, at least one type of storage medium selected from among a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk.

The memory 1300 may store an interactive artificial assistant module including instructions of generating a response message by recognizing a health state of the user from the voice input of the user and analyzing health data pre-stored in the storage 1400. The interactive artificial assistant module may be software including instructions and program codes readable by the processor 1200. According to an embodiment below, the processor 1200 may be implemented by executing the instructions or program codes of the interactive artificial assistant module stored in the memory 1300.

The interactive artificial assistant module may include an ASR model 1310, an NLU model 1320, an NLG model 1330, and a TTS model 1340.

The processor 1200 may control the communication interface 1100 to receive an audio signal from the device 2000. The processor 1200 may perform ASR by using data regarding the ASR model 1310 stored in the memory 1300, and may convert the audio signal received from the device 2000 into text.

The processor 1200 may interpret the text by using data regarding the NLU model 1320 stored in the memory 1300, and may recognize the health state of the user, based on a result of the interpretation. According to an embodiment, the processor 1200 may parse the text in units of morphemes, words, or phrases by using data regarding the NLU model 1320 stored in the memory 1300, and may infer the meaning of a word extracted from the parsed text by using linguistic characteristics (e.g., a syntactic element) of the parsed morpheme, word, or phrase. The processor 1200 may infer the health state of the user by comparing the inferred meaning of the word with pre-defined words provided by the NLU model 1320. The health state of the user may be a word or phrase representing a current health state of the user, such as 'I'm tired', 'My legs hurt', or 'I'm sleepy now~'.

The processor 1200 may analyze health data related to the health state of the user recognized by using the data regarding the NLU model 1320, from among the health data pre-stored in the storage 1400. The health data refers to data representing health information of the user and condition information of the user. The health data may include, for example, at least one type from among the number of steps taken by the user, a sleep duration of the user, a heart rate thereof, or an exercise amount thereof. The health data may be obtained by the device 2000 of the user, and may be transmitted to the server 1000 together with the ID information of the device 2000 (e.g., device ID) and the account information of the user (e.g., user ID). The health data of the user transmitted to the server 1000 may be accumulated for each type and stored in the storage 1400.

The processor 1200 may determine one type from among biometric information, exercise information, and sleep information of the user from the text, by using the data regarding the NLU model 1320, and may obtain a value of health data corresponding to the determined type from among the health data pre-stored in the storage 1400.

The processor 1200 may analyze health data associated with the recognized health state from among a plurality of types of health data pre-stored in the storage 1400. According to an embodiment, the processor 1200 may obtain from the storage 1400 recent health data for a time point before a first time preset from the moment when the device 2000 receives the voice input, from among the pre-stored health data, and calculate an average value of health data during a time section between a time point before a second time preset from the moment when the device 2000 receives the voice input and a time point before a third time preset from the moment when the device 2000 receives the voice input, from among the pre-stored health data, thereby obtaining accumulated health data. The first time may be, for example 24 hours, and the time section between the second time and the third time may be, for example, one week. According to an embodiment, the processor 1200 may obtain, from the storage 1400, recent health data as health data before 24 hours from the moment when the voice input of the user is received from among the health data pre-stored in the storage 1400, and accumulated health data as health data accumulated during one week from the moment when the voice input of the user is received.

The processor 1200 may obtain health state change information of the user by comparing the recent health data with the accumulated health data. According to an embodiment, the processor 1200 may obtain recent health data including information of the user and condition information thereof for each type of health data, such as the number of steps, a sleep duration, a heart rate, and an exercise amount before 24 hours from the moment when the voice input of the user is received, and may analyze the change degree of health data by comparing the obtained recent health data with accumulated health data for one week.

The processor 1200 may compare the recent health data with the accumulated health data for each of the plurality of types of health data, and may analyze the change degree of health data for each of the plurality of types. According to an embodiment, the processor 1200 may determine a type for which the recent health data and the accumulated health data are maximally different, from among a plurality of types of health data, by comparing the recent health data and the accumulated health data for each of the plurality of types with each other. According to an embodiment, the processor 1200 may calculate a difference between the recent health data and the accumulated health data for each of the plurality of types, and may determine a type for which the calculated difference is maximum from among the plurality of types.

According to an embodiment, the processor 1200 may calculate a changing rate of the health data by dividing the differences calculated for the plurality of types of the health data by the respective accumulated health data of the plurality of types. In this case, the processor 1200 may determine a type for which the calculated changing rate is maximum.

The processor 1200 may obtain change information of health data corresponding to the determined type. According to an embodiment, the processor 1200 may determine whether the recent health data of the determined type has increased or decreased compared with the accumulated health data. For example, when the type for which a difference of the health data is maximum is the number of steps, the processor 1200 may determine whether the number of recent steps, namely, the number of steps taken yesterday, has increased or decreased compared with an accumulated number of steps, namely, an average of the number of steps during one week.

The processor 1200 may generate a response message including a first message regarding the health state and the analyzed health data, a second message providing emotional consolation to the user, and a third message proposing a follow-up action associated with the analyzed health data, by using the data regarding the NLG model 1330. According to an embodiment, the first message may be generated based on the information of the user and the condition information according to the health state and the type of health data, such as the number of steps, a sleep duration, a heart rate, and an exercise amount. According to an embodiment, the first message may include information about an increase or decrease in the value of the recent health data compared with the accumulated health data.

The second message may include text and a graphic image. According to an embodiment, the processor 1200 may generate the second message by combining a graphic image corresponding to the contents of a consolation message with the consolation message. According to an embodiment, the processor 1200 may generate the second message by randomly extracting one consolation message from consolation messages pre-stored in the storage 1400.

The third message may include a message that proposes a follow-up action associated with at least one of the types of analyzed health data, for example, the number of steps, a sleep duration, a heart rate, and an exercise amount. According to an embodiment, the processor 1200 may generate the third message proposing a follow-up action, based on an increase or decrease in the value of the recent health data compared with the accumulated health data.

The processor 1200 may interpret the text into which the voice input of the user is converted, by using the data regarding the NLU model 1320, in order to recognize whether the contents of the text is related to an event and is an event type that utilizes the frequency of the event. According to an embodiment, the processor 1200 may parse the text in units of morphemes, words, or phrases by using the data regarding the NLU model 1320, and may infer the meaning of a word extracted from the parsed text by using linguistic characteristics (e.g., a syntactic element) of the parsed morpheme, word, or phrase. The processor 1200 may determine an event type corresponding to the inferred meaning of the word by comparing the inferred meaning of the word with pre-defined event types provided by the NLU model 1320.

When the processor 1200 recognizes that the contents of the text are an event type that utilizes the frequency of the event, the processor 1200 may analyze the frequency of the event type, based on user data. The processor 1200 may generate a reaction message that utilizes the frequency of each event type, by using the data regarding the NLG model 1330. According to an embodiment, the processor 1200 may generates a response message by combining an operation execution completion notifying message with the reaction message.

The processor 1200 may interpret the text into which the voice input of the user is converted, by using the data regarding the NLU model 1320, in order to determine whether the contents of the text correspond to a category that utilizes schedule calculation. According to an embodiment, the processor 1200 may previously define an event type that calculates a certain frequency. The processor 1200 may parse the text in units of morphemes, words, or phrases by using the data regarding the NLU model 1320, and may infer the meaning of a word extracted from the parsed text by using linguistic characteristics (e.g., a syntactic element) of the parsed morpheme, word, or phrase. The processor 1200 may infer the contents about event information from among the words included in the text. The processor 1200 may determine whether the contents of the text correspond to the category that utilizes schedule calculation, by comparing the inferred event information with the pre-defined event type.

When the contents of the text correspond to the category that utilizes schedule calculation, the processor 1200 may recognize whether a joy event schedule to be calculated exists within a corresponding time period. The joy event may refer to a pleasant event capable of offsetting a negative emotion of a user within a preset time period from the moment when a voice input of the user is received. When a joy event schedule exists within the preset time period from the moment when the voice input of the user is received, the processor 1200 may identify the schedule and generate a response message conforming to the category. According to an embodiment, the processor 1200 may generate a response message by using the data regarding the NLG model 1330. The response message may include a joy event information providing message and an emotional reaction message.

When it is determined that the text includes no event information corresponding to the category that utilizes schedule calculation, the processor 1200 may randomly select a message from an utterance set pre-stored in the storage 1400 and generates a response message by using the selected message. Also, when it is determined that there are no event schedules within a preset time period from the moment when the voice input of the user is received, the processor 1200 may randomly select a message from an utterance set pre-stored in the storage 1400 and generates a response message by using the selected message.

The processor 1200 may convert a response message composed of text or a combination of text with a graphic image into an audio signal by using the data regarding the TTS model 1340.

The processor 1200 may control the communication interface 1100 to transmit the generated response message to the device 2000.

The storage 1400 may include at least one storage medium selected from among a flash memory type, a hard disk type, a multimedia card micro type, and a card type memory (for example, a secure digital (SD) or extreme digital (XD) memory).

The storage 1400 may store health data of the user. The server 1000 may obtain health data including at least one of the number of steps taken by the user, a sleep duration of the user, a heart rate thereof, and an exercise amount thereof from the device 2000, and may store the obtained health data to the storage 1400. According to an embodiment, the server 1000 may also obtain device ID information of the device 2000 (e.g., a device ID), and account information of the user of the device 2000 (e.g., a user ID) when obtaining health data from the device 2000, and may store the health data in the storage 1400, according to the device ID information and the account information of the user.

The storage 1400 may classify the health data of the user into a plurality of types, and may store the health data according to the classified types. The storage 1400 may store the health data according to at least one type from among the number of steps taken by the user, a sleep duration of the user, a heart rate thereof, or an exercise amount thereof. The storage 1400 may store information about a time and a date when the health data is stored, together with the health data.

The storage 1400 may store an utterance set. According to an embodiment, the storage 1400 may store a plurality of consolation messages. The consolation messages may be messages that provide emotional consolation to the user. For example, the storage 1400 may include consolation messages such as 'Cheer up', 'Patting', 'It will be okay', and 'Go for it'. The storage 1400 may store graphic images (e.g., an emoticon) related to the consolation messages.

The storage 1400 may include the DB 1410 of FIG. 10 that stores event information representing the frequency of an event for each type of event. The DB 1410 may store a frequency-related event including at least one of a travel, an exercise, a meeting, a conference, a birthday, and a wedding anniversary, for each type.

The storage 1400 may also store a reaction message that provides an emotional reaction to the user.

FIG. 17 is a block diagram of a structure of a device 2000 according to an embodiment of the present disclosure. The device 2000 of FIG. 17 may be the same device as the device 2000 of FIG. 16. The device 2000 of FIG. 17 may include more components than those of the device 2000 of FIG. 16.

In FIGS. 1 through 16, an operation or function of converting a voice input of a user into text and generating a response message by using the text is performed by the server 1000. However, embodiments are not limited thereto. According to an embodiment of the present disclosure, all operations or functions that are performed by the server 1000 may also be performed by the device 2000.

Referring to FIG. 17, the device 2000 may include a user input interface 2100, an output interface 2200, a processor 2300, a sensing unit 2400, a communication interface 2500, an audio/video (NV) input interface 2600, a memory 2700, and a storage 2800.

The user input interface 2100 denotes means via which the user inputs data for controlling the device 2000. For example, the user input interface 2100 may be, but is not limited to, a key pad, a dome switch, a touch pad (e.g., a capacitive overlay type, a resistive overlay type, an infrared beam type, an integral strain gauge type, a surface acoustic wave type, a piezo electric type, or the like), a jog wheel, or a jog switch.

The user input interface 2100 may request a response input for an inquiry message and may receive the response input from a user.

The output interface 2200 may output an audio signal, a video signal, or a vibration signal, and may include a display 2210, an audio output interface 2220, and a vibration motor 2230.

The display 2210 displays information that is processed by the device 2000. According to an embodiment, the display 2210 may receive a response message from the server 1000 and may display the response message. According to an embodiment, the display 2210 may display a response message generated by the processor 2300. The display 2210 may display a response message including text and a GUI. According to an embodiment, the display 2210 may display an operation execution notifying message representing a result of operation execution.

The audio output interface 2220 may output a response message received from the server 1000 through the communication interface 2500 or generated by the processor 2300. According to an embodiment, the audio output interface 2220 may output an audio signal generated by the processor 2300 converting a response message composed of text by using data regarding a TTS model 2718. The audio output interface 1220 also outputs a sound signal related to an operation or function that is performed by the device 2000.

The processor 2300 typically controls all operations of the device 2000. For example, the processor 2300 may control the user input interface 2100, the output interface 2200, the sensing unit 2400, the communication interface 2500, the AN input interface 2600, and the like by processing data stored in the memory 2700 by executing programs stored in the memory 2700. The processor 2300 may perform an operation or function by processing the data stored in the memory 2700 by executing the programs stored in the memory 2700.

The processor 2300 may include, but is not limited to, at least one of, for example, a central processing unit, a microprocessor, a graphic processing unit, application specific integrated circuits (ASICs), digital signal processors (DSPs), digital signal processing devices (DSPDs), programmable logic devices (PLDs), and field programmable gate arrays (FPGAs).

In detail, the processor 2300 may receive a voice input from a user. For example, the processor 2300 may receive the voice input from the user through the microphone 2620. The processor 2300 may perform ASR by using data regarding an ASR model 2712 stored in the memory 2700, and may convert the voice input received from the user into text.

The processor 2300 may interpret the text by using data regarding the NLU model 2714 stored in the memory 2700, and may recognize the health state of the user, based on a result of the interpretation. According to an embodiment, the processor 2300 may parse the text in units of morphemes, words, or phrases by using data regarding an NLU model 2714 stored in the memory 2700, and may infer the meaning of a word extracted from the parsed text by using linguistic characteristics (e.g., a syntactic element) of the parsed morpheme, word, or phrase. The processor 2300 may infer the health state of the user by comparing the inferred meaning of the word with pre-defined words provided by the NLU model 2714.

The processor 2300 may analyze health data related to the health state of the user recognized by using the data regarding the NLU model 2714, from among the health data pre-stored in the storage 2800. The health data refers to data representing health information of the user and condition information of the user. The health data may include, for example, at least one type from among the number of steps taken by the user, a sleep duration of the user, a heart rate thereof, or an exercise amount thereof. The processor 2300 may determine one type from among biometric information, exercise information, and sleep information of the user from the text, by using the data regarding the NLU model 2714, and may obtain a value of health data corresponding to the determined type from among the health data pre-stored in the storage 2800.

The processor 2300 may analyze health data associated with the recognized health state from among a plurality of types of health data pre-stored in the storage 2800. According to an embodiment, the processor 2300 may obtain from the storage 2800 recent health data for a time point before a first time preset from the moment when the voice input is received from the user, from among the pre-stored health data, and calculate an average value of health data during a time section between a time point before a second time preset from the moment when the voice input is received from the user and a time point before a third time preset from the moment when the voice input is received from the user, from among the pre-stored health data, thereby obtaining accumulated health data. The first time may be, for example 24 hours, and the time section between the second time and the third time may be, for example, one week. According to an embodiment, the processor 2300 may obtain, from the storage 2800, recent health data as health data before 24 hours from the moment when the voice input of the user is received from among the health data pre-stored in the storage 2800, and accumulated health data as health data accumulated during one week from the moment when the voice input of the user is received.

The processor 2300 may obtain health state change information of the user by comparing the recent health data with the accumulated health data. According to an embodiment, the processor 2300 may obtain recent health data including information of the user and condition information thereof for each type of health data, such as the number of steps, a sleep duration, a heart rate, and an exercise amount before 24 hours from the moment when the voice input of the user is received, and may analyze the change degree of health data by comparing the obtained recent health data with accumulated health data for one week.

The processor 2300 may compare the recent health data with the accumulated health data for each of the plurality of types of health data, and may analyze the change degree of health data for each of the plurality of types. According to an embodiment, the processor 2300 may determine a type for which the recent health data and the accumulated health data are maximally different, from among a plurality of types of health data, by comparing the recent health data and the accumulated health data for each of the plurality of types with each other. According to an embodiment, the processor 2300 may calculate a difference between the recent health data and the accumulated health data for each of the plurality of types, and may determine a type for which the calculated difference is maximum from among the plurality of types.

According to an embodiment, the processor 2300 may calculate a changing rate of the health data by dividing the differences calculated for the plurality of types of the health data by the respective accumulated health data of the plurality of types. In this case, the processor 2300 may determine a type for which the calculated changing rate is maximum.

The processor 2300 may obtain change information of health data corresponding to the determined type. According to an embodiment, the processor 2300 may determine whether the recent health data of the determined type has increased or decreased compared with the accumulated health data. For example, when the type for which a difference of the health data is maximum is the number of steps, the processor 2300 may determine whether the number of recent steps, namely, the number of steps taken yesterday, has increased or decreased compared with an accumulated number of steps, namely, an average of the number of steps during one week.

The processor 2300 may generate a response message including a first message regarding the health state and the analyzed health data, a second message providing emotional consolation to the user, and a third message proposing a follow-up action associated with the analyzed health data, by using data regarding an NLG model 2716. According to an embodiment, the first message may be generated based on the information of the user and the condition information according to the health state and the type of health data, such as the number of steps, a sleep duration, a heart rate, and an exercise amount. According to an embodiment, the first message may include information about an increase or decrease in the value of the recent health data compared with the accumulated health data.

The second message may include text and a graphic image. According to an embodiment, the processor 2300 may generate the second message by combining a graphic image corresponding to the contents of a consolation message with the consolation message. According to an embodiment, the processor 2300 may generate the second message by randomly extracting one consolation message from consolation messages pre-stored in the storage 2800.

The third message may include a message that proposes a follow-up action associated with at least one of the types of analyzed health data, for example, the number of steps, a sleep duration, a heart rate, and an exercise amount. According to an embodiment, the processor 2300 may generate the third message proposing a follow-up action, based on an increase or decrease in the value of the recent health data compared with the accumulated health data.

The processor 2300 may interpret the text into which the voice input of the user is converted, by using the data regarding the NLU model 2714, in order to recognize whether the contents of the text is related to an event and is an event type that utilizes the frequency of the event. According to an embodiment, the processor 2300 may parse the text in units of morphemes, words, or phrases by using the data regarding the NLU model 2714, and may infer the meaning of a word extracted from the parsed text by using linguistic characteristics (e.g., a syntactic element) of the parsed morpheme, word, or phrase. The processor 2300 may determine an event type corresponding to the inferred meaning of the word by comparing the inferred meaning of the word with pre-defined event types provided by the NLU model 2714.

When the processor 2300 recognizes that the contents of the text are an event type that utilizes the frequency of the event, the processor 1200 may analyze the frequency of the event type, based on user data. The processor 2300 may generate a reaction message that utilizes the frequency of each event type, by using the data regarding the NLG model 2714. According to an embodiment, the processor 2300 may generates a response message by combining an operation execution completion notifying message with the reaction message.

The processor 2300 may interpret the text into which the voice input of the user is converted, by using the data regarding the NLU model 2714, in order to determine whether the contents of the text correspond to a category that utilizes schedule calculation. According to an embodiment, the processor 2300 may previously define an event type that calculates a certain frequency. The processor 2300 may parse the text in units of morphemes, words, or phrases by using the data regarding the NLU model 2714, and may infer the meaning of a word extracted from the parsed text by using linguistic characteristics (e.g., a syntactic element) of the parsed morpheme, word, or phrase. The processor 2300 may infer the contents about event information from among the words included in the text. The processor 2300 may determine whether the contents of the text correspond to the category that utilizes schedule calculation, by comparing the inferred event information with the pre-defined event type.

When the contents of the text correspond to the category that utilizes schedule calculation, the processor 2300 may recognize whether a joy event schedule to be calculated exists within a corresponding time period. The joy event may refer to a pleasant event capable of offsetting a negative emotion of a user within a preset time period from the moment when a voice input of the user is received. When a joy event schedule exists within the preset time period from the moment when the voice input of the user is received, the processor 2300 may identify the schedule and generate a response message conforming to the category. According to an embodiment, the processor 2300 may generate a response message by using the data regarding the NLG model 2716. The response message may include a joy event information providing message and an emotional reaction message.

When it is determined that the text includes no event information corresponding to the category that utilizes schedule calculation, the processor 2300 may randomly select a message from an utterance set pre-stored in the storage 2800 and generates a response message by using the selected message. Also, when it is determined that there are no event schedules within a preset time period from the moment when the voice input of the user is received, the processor 2300 may randomly select a message from an utterance set pre-stored in the storage 2800 and generates a response message by using the selected message.

The processor 2300 may convert a response message composed of text or a combination of text with a graphic image into an audio signal by using the data regarding the TTS model 2718.

The processor 2300 may perform all of the other operations that are performed by the server 1000 of FIGS. 1 through 16.

The sensing unit 2400 may sense the status of the device 2000 or the status of the surrounding of the device 2000 and may transmit information corresponding to the sensed status to the processor 2300. The sensing unit 2400 may be used to generate location information of the user or the device 2000.

The sensing unit 2400 may include, but is not limited thereto, at least one selected from a magnetic sensor 2410, an acceleration sensor 2420, a temperature/humidity sensor 2430, an infrared sensor 2440, a gyroscope sensor 2450, a position sensor (e.g., a global positioning system (GPS)) 2460, a pressure sensor 2470, a proximity sensor 2480, and an RGB sensor 2490 (i.e., an illumination sensor). Functions of most of the sensors would be instinctively understood by one of ordinary skill in the art in view of their names and thus detailed descriptions thereof will be omitted herein.

For example, the device 2000 may obtain the location information of the device 2000 by using the position sensor 2460. For example, the location information may represent the coordinate of a place or location where the device 2000 is current positioned.

The communication interface 2500 may include one or more components that enable the device 2000 to perform data communication with another device and/or the server 1000. The communication interface 2500 may perform data communication with the other device and/or the server 1000 by using at least one of data communication methods including, for example, a wired LAN, a wireless LAN, Wi-Fi, Bluetooth, Zigbee, Wi-Fi Direct (WFD), infrared Data Association (IrDA), Bluetooth Low Energy (BLE), near field communication (NFC), wireless broadband Internet (Wibro), World Interoperability for Microwave Access (WiMAX), a shared wireless access protocol (SWAP), wireless gigabit alliance (WiGig), and RF communication.

For example, the communication interface 2500 may include a short-range wireless communication interface 2510, a mobile communication interface 2520, and a broadcasting receiver 2530.

Examples of the short-range wireless communication interface 2510 may include, but are not limited to, a Bluetooth communication interface, a Bluetooth Low Energy (BLE) communication interface, a near field communication (NFC) interface, a wireless local area network (WLAN) (e.g., Wi-Fi) communication interface, a ZigBee communication interface, an infrared Data Association (IrDA) communication interface, a Wi-Fi direct (WFD) communication interface, an ultra-wideband (UWB) communication interface, and an Ant+ communication interface.

According to an embodiment, the device 2000 may obtain the location information of the device 2000 through the short-range wireless communication interface 2510. For example, the device 2000 may determine the place where the device 2000 is positioned, through an NFC tag. For example, the device 2000 may determine the place where the device 2000 is positioned, through the identifier of Wi-Fi. For example, the device 2000 may ascertain the place where the device 2000 is positioned, by checking an SSID of Wi-Fi to which the device is connected.

The mobile communication interface 2520 may exchange a wireless signal with at least one selected from a base station, an external terminal, and a server on a mobile communication network. Here, examples of the wireless signal may include a voice call signal, a video call signal, and various types of data according to text/multimedia messages transmission.

The broadcasting receiver 2530 receives a broadcasting signal and/or broadcasting-related information from an external source via a broadcasting channel. The broadcasting channel may be a satellite channel, a ground wave channel, or the like. According to embodiments, the device 2000 may not include the broadcasting receiver 2530.

The A/V input interface 2600 inputs an audio signal or a video signal, and may include a camera 2610 and a microphone 2620. The camera 2610 may acquire an image frame, such as a still image or a moving picture, via an image sensor in a video call mode or a photography mode. An image captured via the image sensor may be processed by the processor 2300 or a separate image processor (not shown).

The microphone 2620 receives an external audio signal and converts the external audio signal into electrical audio data. For example, the microphone 2620 may receive a voice input from the user. The microphone 2620 may receive a voice input of the user. The microphone 2620 may use various noise removal algorithms in order to remove noise that is generated while receiving the external audio signal.

The memory 2700 may include at least one type of storage medium selected from among a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk.

The memory 2700 may include an interactive artificial assistant module 2710, a user interface (UI) module 2720, a touch screen module 2730, and a notification module 2740. The interactive artificial assistant module 2710 may store the data regarding the ASR model 2712, the NLU model 2714, the NLG model 2716, and the TTS model 2718.

The UI module 2720 may provide a UI, GUI, or the like that is specialized for each application and interoperates with the device 2000.

The touch screen module 2730 may detect a touch gesture on a touch screen of a user and transmit information regarding the touch gesture to the processor 2300. The touch screen module 2730 according to an embodiment may recognize and analyze a touch code. The touch screen module 2730 may be configured by separate hardware including a controller.

The notification module 2740 may generate a signal for notifying that an event has been generated in the device 2000. Examples of the event generated in the device 2000 may include call signal receiving, message receiving, a key signal input, schedule notification, and the like. The notification module 2740 may output a notification signal in the form of a video signal via the display 2210, in the form of an audio signal via the audio output interface 2220, or in the form of a vibration signal via the vibration motor 2230.

The server 1000 or the device 2000 described above may be implemented as a hardware component, a software component, and/or a combination of hardware components and software components. For example, the server 1000 or device 2000 described in the above embodiments may be implemented using at least one general-use computer or special-purpose computer, such as, a processor, an arithmetic logic unit (ALU), a digital signal processor, a microcomputer, a field programmable array (FPGA), a programmable logic unit (PLU), a microprocessor, or any other device capable of executing and responding to instructions.

The software may include a computer program, a code, instructions, or a combination of one or more of the foregoing, and may configure a processing device so that the processing device can operate as desired, or may independently or collectively give instructions to the processing device.

The software may be implemented as a computer program including instructions stored in computer-readable storage media. Examples of the computer-readable recording media include magnetic storage media (e.g., read-only memory (ROM), random-access memory (RAM), floppy disks, hard disks, etc.), and optical recording media, (e.g., compact disc-ROM (CD-ROM) and digital versatile discs (DVDs)). The computer-readable recording media can also be distributed over network coupled computer systems so that the computer readable code is stored and executed in a distributive manner. This media can be read by a computer, stored in a memory, and executed by a processor.

The computer is a device capable of calling stored instructions from a storage medium and operating according to the disclosed embodiments according to the called instructions, and may include the server 1000 or the device 2000 according to the disclosed embodiments.

The computer-readable storage media may be provided as non-transitory storage media. Here, 'non-transitory' means that a storage medium does not include a signal and is tangible, but does not include distinguish whether data is stored semi-permanently or temporarily in the storage medium.

Also, the server 1000, the device 2000, or operation methods thereof according to the disclosed embodiments may be provided in a computer program product. The computer program product may be traded as a commodity between a seller and a purchaser.

The computer program product may include a software program and a computer-readable storage medium having the software program stored thereon. For example, the computer program product may include a product in the form of a software program (e.g., a downloadable app) that is electronically distributed through the manufacturer of the server 1000 or the device 2000 or an electronic market (e.g., Google Play Store or AppStore). For electronic distribution, at least a portion of the software program may be stored on a storage medium or may be created temporarily. In this case, the storage medium may be a server of a manufacturer, a server of an electronic market, or a storage medium of a relay server for temporarily storing a software program.

The computer program product may include, in a system including a server and a terminal (e.g., a device), a storage medium of the server or a storage medium of the terminal. Alternatively, if there is a third device (e.g., a smartphone) in communication with the server or the device, the computer program product may include a storage medium of the third device. Alternatively, the computer program product may include the software program itself transmitted from the server to the terminal or the third device, or transmitted from the third device to the terminal.

In this case, one of the server, the device, and the third device may execute the computer program product to perform the methods according to the disclosed embodiments. Alternatively, at least two of the server, the device, and the third device may execute the computer program product to distribute and perform the methods according to the disclosed embodiments.

For example, a server (e.g., a cloud server or an AI server) may execute a computer program product stored on a server to control a terminal communicating with the server to perform the methods according to the disclosed embodiments.

As another example, a third device may execute a computer program product to control a terminal in communication with the third device to perform the methods according to the disclosed embodiments.

When the third device executes the computer program product, the third device may download the computer program product from the server and execute the downloaded computer program product. Alternatively, the third device may execute a computer program product provided in a preloaded state to perform methods according to the disclosed embodiments.

In addition, although embodiments of the present disclosure have been illustrated and described above, the present disclosure is not limited to the specific embodiments described above, and various modifications may be made by those of ordinary skill in the art to which the present disclosure pertains without departing from the gist of the present disclosure claimed in the claims. These modifications should not be individually understood from the technical spirit or perspective of the present disclosure.

While the disclosure has been particularly shown and described with reference to examples thereof, it will be understood by those of ordinary skill in the art that various changes in form and details may be made therein without departing from the spirit and scope of the disclosure as defined by the following claims. For example, an appropriate result may be attained even when the above-described techniques are performed in a different order from the above-described method, and/or components, such as the above-described server 1000, device 2000, structure, and circuit, are coupled or combined in a different form from the above-described methods or substituted for or replaced by other components or equivalents thereof.

The invention claimed is:

1. A method, performed by a server, of providing a response message for a voice input of a user, the method comprising:
   receiving a voice input of a user from a device;
   converting the received voice input into text by performing automatic speech recognition (ASR);
   recognizing a health state of the user by interpreting the text by using a natural language understanding (NLU) model;
   analyzing health data associated with the recognized health state from among pre-stored health data of the user;
   generating a response message including a first message regarding the recognized health state and the analyzed health data, a second message providing emotional consolation to the user, and a third message proposing a follow-up action associated with the analyzed health data, by using a natural language generator (NLG); and
   providing the generated response message to the device so that the generated response message is output through the device.

2. The method of claim 1, wherein the analyzing of the health data comprises:
   obtaining recent health data regarding a time point before a preset first time from a time point when the voice input has been received, from among the pre-stored health data pre-stored in the server;
   obtaining accumulated health data by calculating an average value of the health data during a time section between the time point when the voice input has been received and a time point before a preset second time from the time point when the voice input has been received, from among the pre-stored health data;
   determining a type of health data having a largest difference between the recent health data and the accumulated health data by comparing the recent health data with the accumulated health data for each of the plurality of types of health data; and
   obtaining change information of health data corresponding to the determined type of health data.

3. The method of claim 2, wherein the first message comprises the change information of the health data corresponding to the determined type of health data.

4. The method of claim 2, wherein the generating of the response message comprises generating the third message proposing the follow-up action associated with the health data of the determined type, based on an increase or decrease in the value of the recent health data compared with the accumulated health data.

5. The method of claim 1, wherein the generating of the response message comprises generating the second message by combining a graphic image corresponding to contents of a consolation message with the consolation message.

6. The method of claim 1, wherein the generating of the response message comprises generating the second message by randomly extracting one consolation message from pre-stored consolation messages.

7. The method of claim 1, wherein the analyzing of the health state comprises determining one type of health data from among biometric information, exercise information, and sleep information of the user from the text by using the NLU model, and the analyzing of the health data comprises obtaining a value of health data corresponding to the determined type of health data from among the pre-stored health data.

8. A server for providing a response message for a voice input of a user, the server comprising:

a communication interface configured to perform data communication with a device;

a storage accumulating and storing health data of the user;

a memory storing a program comprising one or more instructions; and a processor configured to execute the one or more instructions stored in the memory, wherein the processor is configured to control the communication interface to receive the voice input of the user from the device, convert the received voice input into text by using an automatic speech recognition (ASR) model, recognize a health state of the user by interpreting the text by using a natural language understanding (NLU) model;

analyze health data associated with the recognized health state from among the health data of the user pre-stored in the storage, generate a response message including a first message regarding the recognized health state and the analyzed health data, a second message providing emotional consolation to the user, and a third message proposing a follow-up action associated with the analyzed health data, by using a natural language generator (NLG), and provide the generated response message to the device through the communication interface.

9. The server of claim 8, wherein the processor is further configured to obtain recent health data regarding a time point before a preset first time from a time point when the voice input has been received, from among the health data pre-stored in the storage, obtain accumulated health data by calculating an average value of the health data during a time section between the time point when the voice input has been received and a time point before a preset second time from the time point when the voice input has been received, from among the pre-stored health data, determine a type of health data having a largest difference between the recent health data and the accumulated health data by comparing the recent health data with the accumulated health data for each of a plurality of types of health data, and obtain change information of health data corresponding to the determined type of health data.

10. The server of claim 9, wherein the first message comprises the change information of the health data corresponding to the determined type of health data.

11. The server of claim 9, wherein the processor is further configured to generate the third message proposing the follow-up action associated with the health data of the determined type, based on an increase or decrease in the value of the recent health data compared with the accumulated health data.

12. The server of claim 8, wherein the processor is further configured to generate the second message by combining a graphic image corresponding to contents of a consolation message with the consolation message.

13. The server of claim 8, wherein the processor is further configured to generate the second message by randomly extracting one consolation message from consolation messages pre-stored in the storage.

14. The server of claim 8, wherein the processor is further configured to determine one type of health data from among biometric information, exercise information, and sleep information of the user from the text, by using the NLU model, and obtain a value of health data corresponding to the determined type of health data from among the health data pre-stored in the storage.

15. A non-transitory computer-readable recording medium having recorded thereon a computer program, which, when executed by a computer, performs the method of claim 1.

* * * * *